US010281432B2

(12) United States Patent
Zhang et al.

(10) Patent No.: US 10,281,432 B2
(45) Date of Patent: May 7, 2019

(54) DETECTION APPARATUS AND DETECTION METHOD

(71) Applicant: Nuctech Company Limited, Beijing (CN)

(72) Inventors: Qingjun Zhang, Beijing (CN); Yuanjing Li, Beijing (CN); Zhiqiang Chen, Beijing (CN); Ziran Zhao, Beijing (CN); Yinong Liu, Beijing (CN); Yaohong Liu, Beijing (CN); Huishao He, Beijing (CN); Qiufeng Ma, Beijing (CN); Weiping Zhu, Beijing (CN); Xiang Zou, Beijing (CN); Jianping Chang, Beijing (CN); Song Liang, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 15/280,744

(22) Filed: Sep. 29, 2016

(65) Prior Publication Data

US 2017/0016856 A1    Jan. 19, 2017

Related U.S. Application Data

(63) Continuation of application No. PCT/CN2015/098680, filed on Dec. 24, 2015.

(30) Foreign Application Priority Data

Dec. 31, 2014    (CN) .......................... 2014 1 0855312

(51) Int. Cl.
*H01J 49/00* (2006.01)
*G01N 27/62* (2006.01)
(Continued)

(52) U.S. Cl.
CPC ............. *G01N 27/622* (2013.01); *G01N 1/02* (2013.01); *G01N 1/2211* (2013.01); *G01N 1/405* (2013.01);
(Continued)

(58) Field of Classification Search
CPC ........ G01N 27/622; H01J 49/00; H01J 49/02; H01J 49/04; H01J 49/0422; H01J 49/0431;
(Continued)

(56) References Cited

U.S. PATENT DOCUMENTS 5,012,052 A * 4/1991 Hayes ................ G01N 30/7206
250/282
2006/0032071 A1 2/2006 Baba et al.
(Continued)

FOREIGN PATENT DOCUMENTS

CN    1575195 A    2/2005
CN    1720440 A    1/2006
(Continued)

OTHER PUBLICATIONS

Sielemann, S., et al., "Detection of trans-1,2-dichloroethene, trichloroethene and tetrachloroethene using Multi-Capillary Columns Coupled to Ion Mobility Spectrometers with UV-Ionisation Sources," International Journal for Ion Mobility Spectrometry 2(1999)1, pp. 15-21.
(Continued)

*Primary Examiner* — Jason L McCormack
(74) *Attorney, Agent, or Firm* — Knobbe, Martens, Olson & Bear LLP

(57) ABSTRACT

A detection apparatus and a detection method are disclosed. In one aspect, the detection apparatus includes a sampling device for collecting samples to be checked. It further includes a sample pre-processing device configured to pre-process the sample from the sampling device. It further includes a sample analyzing device for separating samples from the pre-processing device and for analyzing the separated samples. The detection apparatus is miniaturized and highly precise, and is capable of quickly and accurately (Continued)

detecting gaseous phase or particulate substances, and it has applications for safety inspections at airports, ports, and subway stations.

5 Claims, 12 Drawing Sheets

(51) Int. Cl.
*H01J 49/04* (2006.01)
*G01N 1/02* (2006.01)
*G01N 1/22* (2006.01)
*G01N 1/40* (2006.01)
G01N 30/60 (2006.01)
G01N 30/72 (2006.01)
G01N 1/42 (2006.01)

(52) U.S. Cl.
CPC ...... *H01J 49/0422* (2013.01); *H01J 49/0459* (2013.01); *H01J 49/0468* (2013.01); G01N 1/42 (2013.01); G01N 30/60 (2013.01); G01N 30/722 (2013.01); G01N 2001/028 (2013.01)

(58) Field of Classification Search
CPC .... H01J 49/044; H01J 49/0445; H01J 49/045; H01J 49/0454; H01J 49/26
USPC .......................................... 250/281, 282, 288
See application file for complete search history.

(56) References Cited

U.S. PATENT DOCUMENTS

| | | | |
|---|---|---|---|
| 2009/0050801 A1* | 2/2009 | Fedorov | H01J 49/066 250/288 |
| 2009/0173879 A1* | 7/2009 | Arii | G01N 27/64 250/282 |
| 2009/0272894 A1* | 11/2009 | Shiokawa | H01J 49/145 250/282 |
| 2011/0114836 A1* | 5/2011 | Prakash | G01N 30/8675 250/282 |
| 2011/0159596 A1 | 6/2011 | Keinan et al. | |

FOREIGN PATENT DOCUMENTS

| | | |
|---|---|---|
| CN | 1910453 A | 2/2007 |
| CN | 101285741 A | 10/2008 |
| CN | 101382526 A | 3/2009 |
| CN | 101728208 A | 6/2010 |
| CN | 201561956 U | 8/2010 |
| CN | 201917559 U | 8/2011 |
| CN | 103487494 A | 1/2014 |
| CN | 203798779 U | 8/2014 |
| CN | 104517799 A | 4/2015 |
| CN | 204424206 U | 6/2015 |
| JP | 2011247609 A | 12/2011 |
| WO | WO 02/060565 A1 | 8/2002 |
| WO | WO 2005/071395 A1 | 8/2005 |

OTHER PUBLICATIONS

Chinese Office Action dated Apr. 25, 2016 for Chinese Application No. 201410855312.0 which corresponds in priority to above-identified subject U.S. application.

International Written Opinion and Search Report dated Mar. 31, 2016 for PCT International Application No. PCT/CN2015/098680 which corresponds in priority to above-identified subject U.S. application.

Partial Supplementary European Search Report for Application No. 15875164.4 dated Aug. 31, 2018, in 15 pages, which corresponds in priority to the above-identified U.S. application.

\* cited by examiner

DETECTION APPARATUS AND DETECTION METHOD

CROSS-REFERENCE TO RELATED APPLICATIONS

This application claims priority to International Application No. PCT/CN2015/098680, filed on Dec. 24, 2015, entitled "DETECTION DEVICE AND DETECTION METHOD", and Chinese Application No. 201410855312.0, filed on Dec. 31, 2014, incorporated herein by reference in their entirety.

BACKGROUND

Field

The disclosed technology relates to the field of safety detecting technology, and in particular, to a detection apparatus and a detection method.

Description of the Related Technology

Ion mobility spectrometry (IMS) enables detection of trace quantities of drugs, explosives, toxic gases, biochemical gases and other substances, with civil, counter terrorism, and military applications. IMS separates and identifies samples based on differences among mobility rates of different ions under the action of a weak electric field. It has the advantages of a simple structure, high sensitivity, fast analysis speed and reliable results. However, IMS is prone to false alarms and missed detects when a complex mixture of components is sampled for detection.

Gas chromatography (GC) is combined with IMS in GC-IMS systems to improve detection resolution. GC-IMScombination technology solves the low identification performance of GC and cross sensitivity issue of IMS when sampling mixtures for improved retention time, drift time and signal intensity to effectively identify the complex components of samples with a detection limit that is superior to part per billion (ppb) order of magnitude and a resolution time from a few minutes to tens of minutes. Compared with other combination technologies, the GC-IMS has the advantages of a simple interface, low maintenance cost, and high cost effectiveness. GC-IMS combination technology is rapidly developing in miniaturized and portable systems for security applications.

IMS and GC-IMS systems acquire samples with a sampling device. Sampling directly affects response sensitivity, instrument use range, and accuracy. IMS systems may use a variety of sampling devices may be used and matched. This technology is mature. GC systems may usea headspace sampling which eliminates the need for complex sample pre-treatment, which is suitable for rapid detection. However, headspace sampling "destructively" obtains a certain amount of sample, so it is not suitable for fast detection on-site of trace gas without unpacking.

SUMMARY OF CERTAIN INVENTIVE ASPECTS

The disclosed technology includes a detection apparatus that overcomes disadvantages existing in the conventional technical solutions.

One aspect is a detection apparatus. The detection apparatus includes a sampling device for collecting a sample to be detected. The detection apparatus further includes a sample pre-processing device configured to pre-process the sample from the sampling device. The detection apparatus further includes a sample analyzing device for separating the sample pre-processed by the sample pre-processing device and analyzing the separated sample.

The detection apparatus may amplify collection of volatile organic compounds (VOCs) or semi-volatile organic compounds (Semi-VOCs) and improve sampling efficiency. The detection apparatus may collect, sample and detect volatile trace substances, semi-volatile trace substances or surface contaminants on-site without unpacking. This one-stop detection technology not only improves detection speed but avoids privacy disputes in safety security It operates like a sniffer dog, which is suitable for on-site rapid detection in the airport, customs and the like. It rapidly detects sampled surface contaminants and gaseous substances by rapid collection, pre-concentrated desorption and separation of the sample without unpacking, thereby greatly improving accuracy and saving sample solution preparation time.

If there are several articles to be detected, a latter article may be sampled and collected while a former article is being analyzed, so that the overall time for sample collection and detection is reduced, throughput and detection speed of the analytical instrument are effectively improved, and cost is saved.

When lower detection limit requirements to the detection instrument (e.g., IMS, mass spectrometry (MS), differential mobility spectrometry (DMS)) are reduced, development difficulty and the cost of the instrument are reduced and the false alarm rate of the instrument is reduced. This has advantages with regard to miniaturization and portability of the instrument. Components separated by the multicapillary columns (MCC) are guided directly into the reaction region in the middle of the dual-mode migration tubes, instead of into the ionization region, which avoids generating molecular and ion fragments and enables the GC-IMS to identify positive and negative ions. As a result, the spectrometer is able to be responsive to both positive and negative electrical affinity of macromolecules, which makes up for shortcomings of the prior art technology and broadens detection material selective range of MCC-IMS analysis unit.

No switching element is required for the MCC-IMS analysis unit, and the ports of the MCC are coupled directly with the IMS unit, which avoids turbulent flow induced due to turn around of the switching element, and effectively improves detection sensitivity and resolution rate of the IMS.

A thermal insulation positioning unit is provided between the MCC and the IMS reaction region base, which has both positioning and thermal insulation functions, is simple in structure, is easy to be mounted and operated, and omits additional provision of the switching element and its temperature controlling system design. The heating elements of the MCC are embedded evenly within the thermal sleeve, and the benefits of this design are that rapid heating of the MCC is achieved, uniform heating of the MCC is ensured, the sample gasification and separation are ensured and separation discrimination is reduced. Coordination and control among thermal sleeves, heat pipes, heating elements, pumps and controllers achieve a programmed heating effect of the MCC. The application field of the MCC-IMS can be extended to cope with the separation of the components of the wide boiling range sample, which improves selective range of the substances to be analyzed.

DETAILED DESCRIPTION OF CERTAIN EMBODIMENTS

Although the disclosed technology permits various modifications and alternatives, exemplary embodiments of the disclosed technology will be shown in the attached drawings and be described as examples in the description in detail. It should be understood that, however, the attached drawings and the detailed description should not be construed as being limited to the embodiment set forth herein; rather, these embodiments are provided to cover all the modification, equivalents and alternatives fallen into the principles and spirit of the disclosed technology, the scope of which is defined in the claims. The attached drawings are for illustration purpose, and are not drawn in scale.

Several embodiments of the disclosed technology will be explained with reference to the attached drawings.

Figure 1:
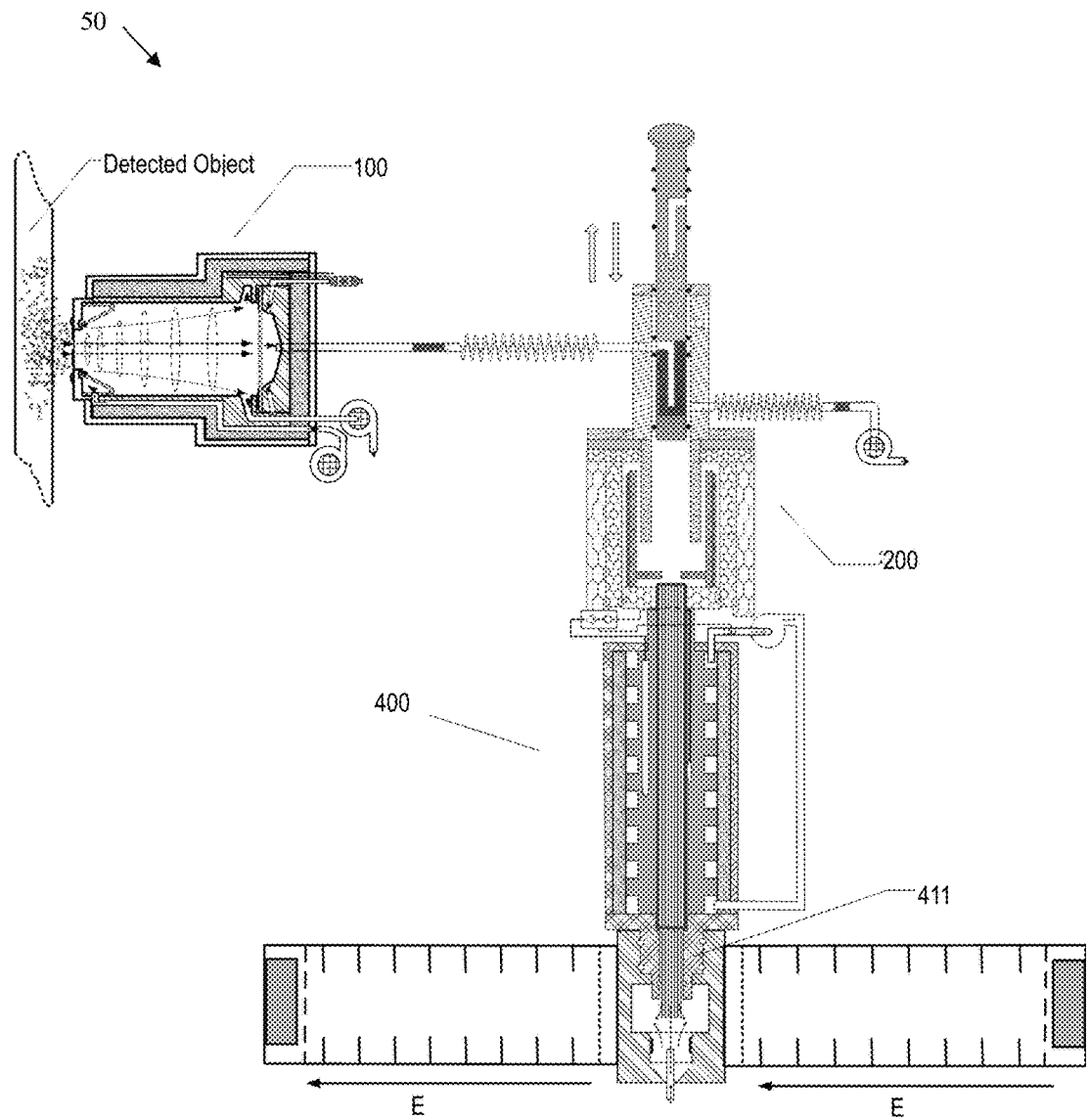
FIG. 1 is a schematic view of a detection apparatus according to the disclosed technology.
Figure 2:
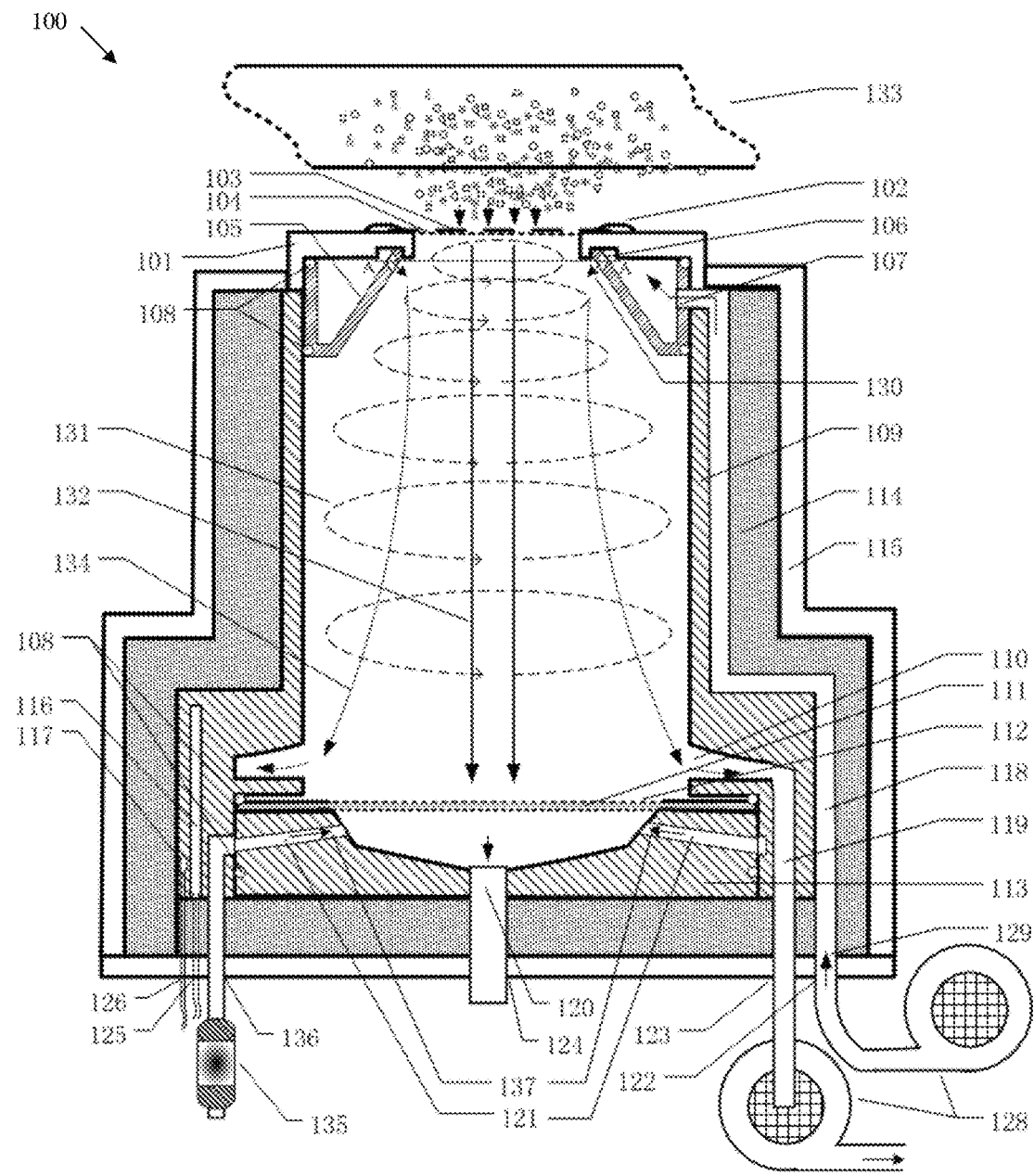
FIG. 2 is a schematic view of a sampling device of a detection apparatus according to an embodiment of the disclosed technology.
Figure 5:
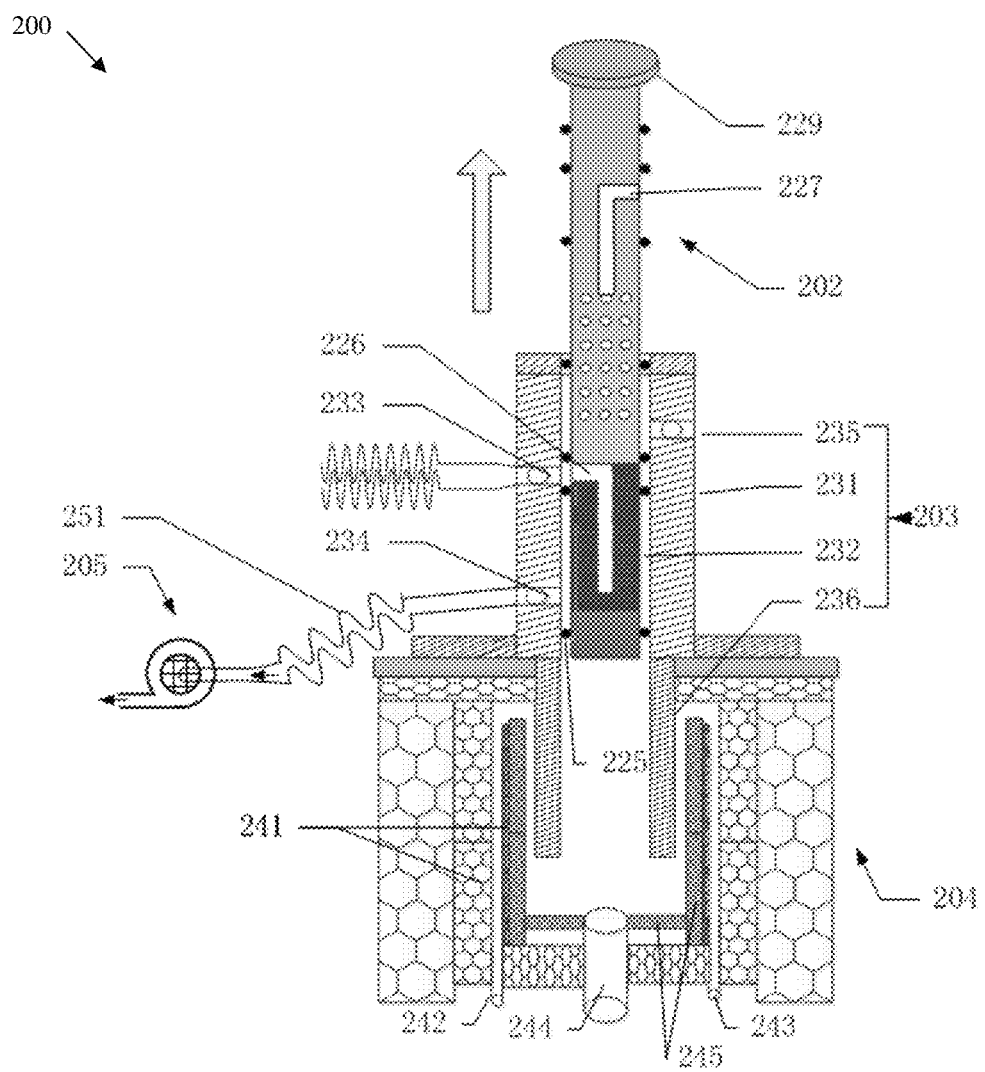
FIG. 5 is a schematic view of a sample pre-processing device according to an embodiment of the disclosed technology.
Figure 8:
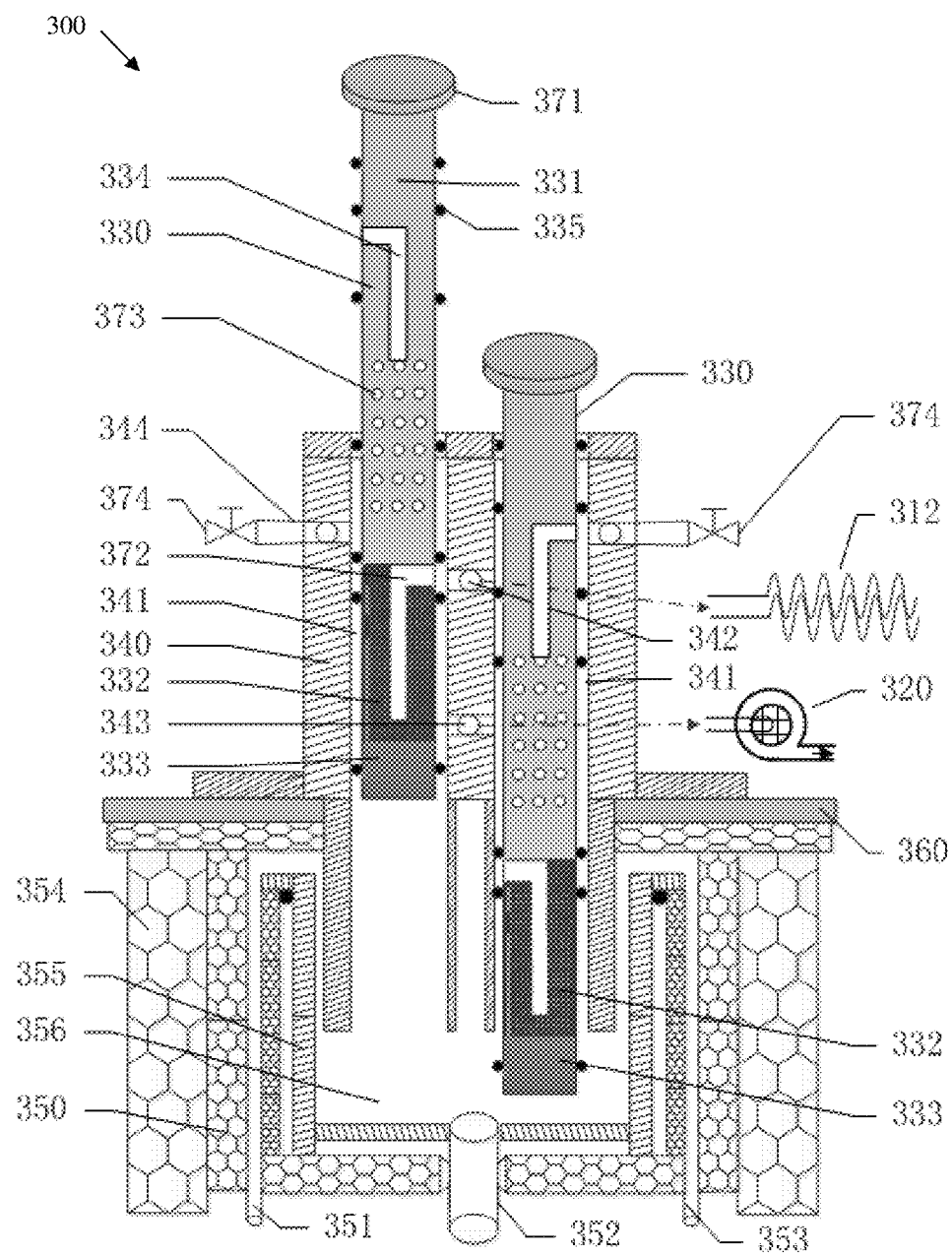
FIG. 8 is a schematic view of a sample pre-processing device according to another embodiment of the disclosed technology.
Figure 9:
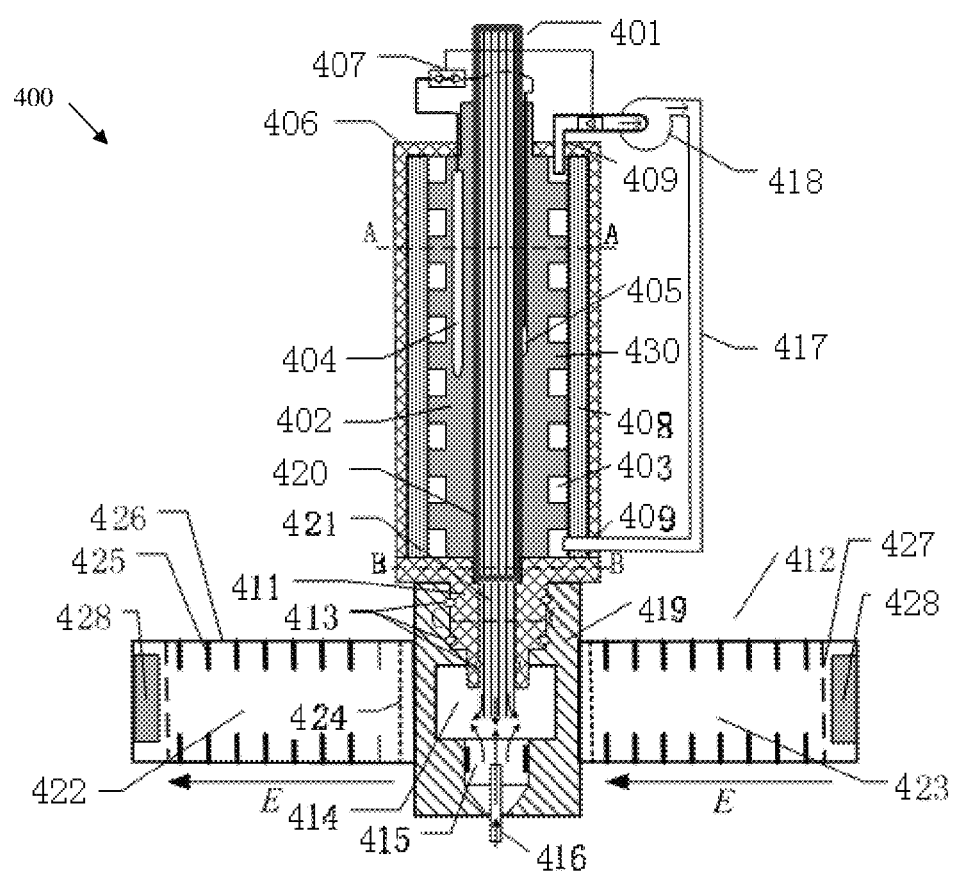
FIG. 9 is a schematic view of a sample analyzing device according to an embodiment of the disclosed technology.

FIG. 1 is a schematic view of a detection apparatus 50. The detection apparatus 50 includes a sampling device 100 for collecting a sample to be detected, a sample pre-processing device 200 configured to pre-process the sample from the sampling device 100, and a sample analyzing device 400 for separating the sample pre-processed by the sample pre-processing device 200 and analyzing the separated sample. The sampling device 100, the sample pre-processing device 200 and the sample analyzing device 400 may be connected and communicate, for example, by bellows. Arrangement of these components of the detection apparatus 50 shown in FIG. 1 is provided for schematic purpose, instead of limiting the disclosed technology. FIGS. 2, 5, and 9 illustrate example embodiments of sample device 100, sample pre-processing device 200 and sample analyzing device 400, respectively. An exemplary embodiment of an alternative sample pre-processing device 300 is illustrated in FIG. 8.

FIG. 2 is a schematic view of a sampling device 100. Sampling device 100 is a tornado type sampling device that generates an artificial tornado for amplified collection of volatile organic compounds (VOCs) and semi-volatile organic compounds (semi-VOCs). Sampling device 100 samples compounds in real time. The sampling device 100 includes an end cap 101 having an aperture and a pressure ring 102 disposed on the end cap 101. A coarse strainer 103 and a fine strainer screen 104 are mounted over the aperture of the end cap 101 by the pressure ring 102 to prevent large particles from entering the sampling device 100. The coarse strainer 103 is sufficiently rigid to bear external environment pressure and the impact of large particles. The fine strainer 104 screen filters out of fine solid particles or micro particles. Alternatively, an integrated end cap 101 having an aperture, also called a sample inlet, may be used. The sample inlet is provided with a porous element, such as coarse filter screen 103 or fine filter screen 104, to prevent large particles from entering the end cap 101.

The sampling device 100 further includes a rotary air curtain guide 105 over which the end cap 101 is closed through an O-type sealing ring 108. In other words, an upper ring-shaped surface of the curtain guide 105 is covered by the O-type sealing ring 108. The rotary air curtain guide 105 has a cylindrical outer wall and also an inner wall having a cross section, for example, of a funnel type shape as shown. In other words, the air curtain guide 105 may be a barrel having a funnel type inner wall. Alternatively, the air curtain guide 105 may be an integrally formed single piece.

An angle between the funnel type inner wall and the cylindrical outer wall may be between 20°~30°, although other values of the angle may be adopted. In an embodiment, a diameter of the lower end face of the funnel type inner wall of the air curtain guide 105 is at least two times of a diameter of the upper end face thereof. In other words, the diameter of the lower opening formed by the funnel type inner wall is at least two times of the diameter of the upper opening. This funnel-type design helps to simulate generation of an artificial tornado within the sampling device 100. An interior space is defined by inner surface of the funnel type inner wall of the air curtain guide 105, that is, the interior space between two inner wall sections of the air curtain guide 105 as shown in the sectional view of FIG. 2.

Figure 3:
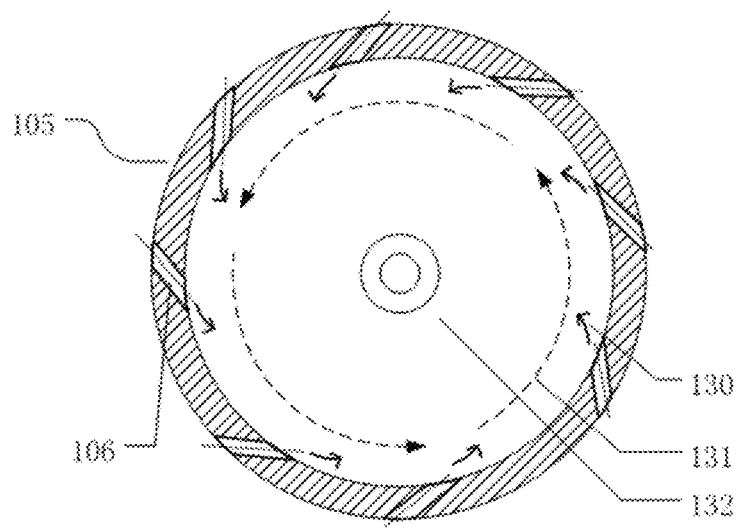
FIG. 3 is a schematic sectional view of an air curtain guide according to an embodiment of the disclosed technology.

FIG. 3 is a schematic sectional view of side wall of an air curtain guide 105 along A-A of FIG. 2. As shown in FIG. 3, a plurality of swirl gas holes 106 are formed evenly at the upper end of the funnel type inner wall of the air curtain guide 105 and have their axial directions close to being tangent with the inner wall of the funnel, and an angle of axial lines of the swirl gas holes 106 relative to a vertical direction is between 45°~90°. Thereby, the swirl gas holes 106 are tangent with the funnel type inner wall of the air curtain guide 105 and face downward (along an arrow direction shown in FIG. 2), such that the gas may go from the swirl gas holes 106 and then flow downward along a direction that is tangent with the funnel type inner wall.

Referring to FIG. 2, an air inflation opening 107 is formed on the cylindrical outer wall of the air curtain guide 105. An annular space is defined by the cylindrical outer wall, the funnel type inner wall of the rotary air curtain guide 105 and the end cap 101. The air may enter the annular space through the air inflation opening 107, and then the air within the annular space is blown into the funnel type interior space of the air curtain guide 105 through the swirl gas holes 106 on the funnel type inner wall, forming a swirl air curtain 130.

In this embodiment, the sample is suctioned at the upper end and is discharged at the lower end, and a flow of inflation gas flows in the downward direction of the arrows spirally. However, it is only one example. When the sampling device 100 is horizontally placed to be in front of an object to be detected, for example, the sample inlet is placed to be in front of an objected to be detected which is located at the left of the sampling device 100, and a side, where the opening with smaller diameter is provided, of the air curtain guide 105 is in front of the object to be detected. Here, the funnel type inner wall 109 is placed transversely and the sample goes from the left to the right.

The air curtain guide 105 may include an inflation passage 118. In FIG. 2, one end of the inflation passage 118 is in fluid communication with with the air inflation opening 107 while the other end is communicated with (in fluid communication with) an air pump 128. The air pump 128 delivers the air into the annular space through inflation passage 118 and the air inflation opening 107, and the air that enters the annular space is blown into the funnel type interior space through the swirl gas holes 106 of the funnel type inner wall, to form a swirl air curtain 130.

The sampling device 100 further includes an air guide chamber 109 having a cylindrical inner wall. The air guide chamber 109 is embedded into the sampling device 100 under the air curtain guide 105 by using an O-ring seal. The air guide chamber 109 may be engaged with the air curtain guide 105 in any other manner as long as the generation of a tornado type air flow within the air guide chamber is not affected. The tornado type air flow is known to those skilled in the art. That is, peripheral gas of an air flow spirally rotates at high speed or at least quickly, so that there is a rotation movement in a horizontal cross-section of the air flow (in a cross-section of the air guide chamber in this embodiment) while there still is a forward movement (from the end of the sample inlet to the end of the sample outlet) in a longitudinal direction, and at the same time, gas at the center of the air flow or at the axis is suctioned forward along the longitudinal direction.

Figure 4:
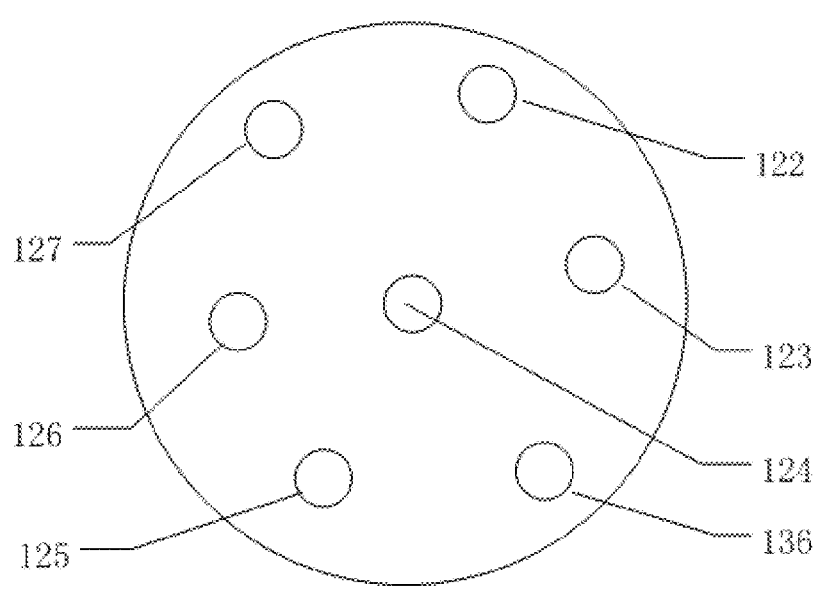
FIG. 4 is a schematic sectional view of a conduit outlet at a bottom surface of a sampling device according to an embodiment of the disclosed technology.

The air guide chamber 109 is configured to maintain a tornado type cyclone and guide the tornado type air-borne substance suctioned along the axis to enter a subsequent detection device. As shown in FIG. 2, the swirl air curtain 130 moves downward, and enters the air guide chamber 109 to form a swirl gas 131. The tornado type swirl gas flow 132 flows in the air guide chamber 109, passes through a swirl gas outlet 110 at the lower side wall of the air guide chamber 109, and then is discharged from the exhaust pump interface 123 and the ventilation outlet 127. The pump interface 123 is a ventilation outlet. In order to increase a ventilation speed, several ventilation outlets may be provided on the bottom end surface. FIG. 4 schematically shows the ventilation outlet 127 which is provided at any position facing the peripheral gas flow 134 of the swirl gas 131, for receiving the peripheral gas flow 134. It may correspond to the 123 and its number may be one or several. Such ventilation outlet 127 is not shown in FIG. 2.

The sampling device 100 further includes a funnel type bottom cap 113 by which a lower end face of the air guide chamber 109 is covered with a O-ring seal 108. A semipermeable membrane 111 is provided between the bottom cap 113 and the lower end opening of the air guide chamber 109 and is provided for preventing water molecules, ammonia molecule and other contaminants in the suctioned VOCs or Semi-VOCs from entering and contaminating subsequent chromatographic column or migration tube. In addition, the semi-permeable membrane 111 may further restrict formation of the cluster, thereby improving a resolution ratio of the apparatus.

In an embodiment, there may be two pieces of network metal 112 for clamping the semi-permeable membrane 111 and protecting it from suffering an air impact.

The funnel type bottom cap 113 may be served as a mixing region or a mixing chamber for the carrier gas and the sample. The funnel type bottom cap 113 may includes a carrier gas passage 121 for infusion of the carrier gas. The infused carrier gas is mixed sufficiently with the sample in the funnel. The funnel type bottom cap 113 may further includes a sample induction opening 120 through which the collected sample and the carrier gas are discharged after the mixing and the preheating and passed to a subsequent analyzing device. In some cases, the carrier gas and the sample may be discharged after being mixed directly without the preheating.

The sampling device 100 further includes a thermal sleeve 114 provided on the air guide chamber 109, and a heating rod 116 and a temperature sensor 117 provided within the air guide chamber 109, the three of which constitute a temperature controlling system that is configured to control temperature of the air guide chamber 109, for example, by heating up. The temperature controlling system may control the temperature inside the chamber body to between 50° C.-250° C., which helps to quickly gasify high boiling VOCs or Semi-VOCs so that they smoothly pass through the semipermeable membrane, and which also helps to sufficiently mix the gasified sample and the carrier gas entered from the carrier gas passage 121 on the funnel type side wall, effectively improving a detection limit of high boiling substrate. After being mixed and preheated with the carrier gas, the collected sample may be brought into the sample induction opening 120. In an embodiment, the rotary air curtain guide 105, the air guide chamber 109 and the bottom cap 113 may be made of metallic material with good thermal performance. In addition, the thermal sleeve 113 may be made of aerogel or glass or ceramic wool which has a thickness of about 10 mm. Optionally, a Teflon outer casing housing 115 may be cased outside the thermal insulation layer 114.

The bottom end face of the outer casing housing 115 may be provided with an inflator pump interface 122, an exhaust pump interface 123, a GC column/ion migration tube interface 124, a heating rod outgoing line 125, a temperature sensor outgoing line 126, a ventilation outlet 127 and a carrier gas tube interface 136, as shown in FIG. 4. The inflator pump interface 122 and the exhaust pump interface 123 may be connected respectively with an air pump 128 for continuously supplying an air pressure so that a tornado type air flow may be formed inside the sampling device 100. The exhaust pump interface 123 may be arranged in a manner to make the air resistance as small as possible, so that the opening of the exhaust pump interface in the air guide chamber faces toward a gas flow on-coming direction, facilitating an easy inflow of the air flow into the exhaust pump interface. The exhaust pump interface 123 may not be connected to the air pump 128 and be served directly as a ventilation outlet. In order to discharge the tornado type suctioned and amplified gas flow, several ventilation outlets 127 may be formed. The GC column/ion migration tube interface 124 may be connected to a pre-processing device 200 or 300, or to the GC column, or directly to the ion migration tube. The carrier gas tube interface 136 may be connected to a molecular sieve 135 so that the carrier gas will be purified.

Power of the air pump 128 as shown may be adjusted as needed. Since the tornado type owns a gas collection and amplification function, a flow ratio of the exhaust pump may be ten times or more as that of the inflator pump.

In order to prevent the interference of an air flow from the inflator pump 128 on the target components suctioned from the sampled object 133, on one hand, an air source for collection by the inflator pump is provided as far as possible from the sampled object 133, for example, using a retractable and flexible conduit to keep the pump far away from the sampling end; on the other hand, the air into the inflator pump is filtered and purified, avoiding cross contamination of the gas and improving sensitivities of locating and sampling performance of the sampling instrument.

Sampling and sample-supplying processes of the sampling device 100, which includes a gas collection and amplification function will be described hereafter.

A front end opening/aperture of the sampling device 100 is placed near a sampled object, that is, in a location that is away from the sampled object by 5-10 cm, to aim at the sampled object 133, while air pump and exhaust air pump 128 are turned on. The inflated air flow 129 is inflated through an inflation tube, and into the annular space of the air curtain guide 105 via the air inflation opening 107. A gas pressure is generated within the annular space under the action of an air pressure continuously applied by the air pump 128. With the action of the gas pressure, the air is blown into interior space of the funnel through the swirl gas holes 106 of the air curtain guide 105. Due to specific construction of the swirl gas holes 106, the air is blown into the interior space in a specific direction, forming a funnel type rotary air curtain 130.

In a case that the air is constantly blown by the air pump 128, the rotary air curtain formed continuously moves along an inner wall of the air guide chamber 109, that is, it rotates quickly around a central axis 132 of the air guide chamber 109 while moving downward, to form a tornado type air flow 131. Under the action of a centrifugal force caused by this rotation, central air pressure of the tornado type air flow reduces remarkably, e.g., air pressure of the central axis 132 is smaller than ambient pressure about ten times, and accordingly, a great suction force may be generated at the central axis 132 of the air guide chamber 109. The suction force makes the air-borne substance in the vicinity of the sampled object 133 to be suctioned to be adjacent to the center of the wind axis within the air guide chamber 109 from the front end aperture of the air guide chamber 109, and to form a sample gas column that moves downwardly along a central axis of the tornado type air flow and finally reaches the sample-supplying semi-permeable membrane 111. This process looks like a tornado phenomenon in the nature.

On one hand, the collected sample enters a funnel chamber of the bottom cap 113 through the semi-permeable membrane 111, and is quickly gasified under a preheated condition and then is mixed sufficiently with the carrier gas flow 137 entered from the carrier gas passage 121 in the side wall of the bottom cap 113. After that, the carrier gas carrying the sample enters the sample-supplying interface 120.

On the other hand, for the gas at the periphery of a rotation center of the tornado type air flow 131, a cyclone formed at the periphery of the tornado type air flow 131 moves along side wall of the air guide chamber 109. At the bottom of the air guide chamber, gas of the peripheral cyclone enters the outlet 110 and forms a vortex flow 134 that will be discharged at the ventilation outlet 127. The outlet 110 is oriented towards a gas flow direction of the cyclone. In the orientation shown in FIG. 2, the outlet 110 may be inclined upward, and, the outlet may deviate towards a tangential direction of the inner wall, instead of being oriented towards a center of the chamber body, facilitating the open oriented direction of the outlet to be much closer to the velocity direction of the gas flow at the outlet. That is to say, although the open oriented direction of the outlet 110 does not reverse strictly the velocity direction of the gas flow at the outlet, it is close to a direction reversing the velocity direction of the gas flow at the outlet, such that the gas will easily enter the outlet 110 and is discharged.

Through this process, the sampling device 100 may constantly suction sample molecules, thereby achieving amplified collection of the air-borne substance.

This tornado type real-time sampling device 100 having the gas amplified collection function may be used directly as a sample-supplier of analytical instruments including IMS, GC, MS, GC-IMS, GC-MS, etc.

Another embodiment of the sampling device according to the disclosed technology will be described hereafter. This embodiment is similar to those mentioned in the above, and only different parts will be described for clarity.

In this embodiment, the sampling device 100 includes a first end and a second end opposite to the first end. The sampling device 100 includes a chamber body 109, and a part 105 of the chamber body has a funnel shape or a truncated conical shape. Specifically, the chamber body has a sample inlet that is adjacent to the first end and is for suction of the sample, and a sample outlet 120 that is adjacent to the second end and is for discharge of the sample. The sample inlet of the chamber body 109 is located adjacent to a smaller-diameter round end of the truncated conical shape inner wall 109, and the larger-diameter round end of the truncated conical shape inner wall 109 is close to the sample outlet.

In other words, the smaller-diameter end of the funnel type inner wall 109 faces the sample, while the larger-diameter end is towards the sample outlet for discharging the sample. The chamber body shown in figure is that the sample inlet faces upwards while the sample outlet for discharging the sample faces downwards, that is, the funnel type chamber body 109 is arranged in an inverted funnel manner. However, it is only one example. When the sampling device 100 is horizontally placed to be in front of an object to be detected, for example, the sample inlet is placed to be in front of an objected to be detected which is located at the left of the sampling device 100, and a side, where the aperture is provided, of the funnel type inner wall 109 is in front of the object to be detected at the left. Here, the funnel type inner wall 109 is placed in a horizontal arrangement manner.

The chamber body is further formed with an air inflation opening 106 configured to induct a flow of air into the chamber body, in order to form a tornado type air flow within the chamber body. The chamber body is further formed with an air exhaust opening configured to discharge the air and to, together with the air inflation opening 106 in the chamber body, form the tornado type air flow. Specifically, the air inflation opening 106 is configured such that an axially air induction direction of the air inflation opening 106 is close to being tangent with an inner surface of the inner wall of the chamber body but is inclined towards a side of the sample outlet. For example, FIG. 3 schematically shows a sectional view along line A-A in FIG. 2.

In this embodiment, the air curtain guide 105 may not be provided alone, and, an arrangement in which the abovementioned air inflation opening 106 and corresponding air inflation passage are provided adjacent to the side of the inner wall close to the sample inlet of the chamber body achieves a similar effect as that of the abovementioned air curtain guide 105. Moreover, an annular space for the air curtain guide, as mentioned in the aforementioned embodiment, may be formed inside the chamber body, and is configured to accommodate the gas therein to create a gas pressure within the annular space, and, the gas is inflated into the interior space of the sampling device 100 through the air inflation opening.

The air exhaust opening 110 is located in wall of the chamber body, and may be arranged in a similar manner to the air exhaust opening in the aforementioned embodiment. The air exhaust opening 110 faces toward the tornado type air flow spirally advanced from the air inflation opening 106, so that the air flow enters the air exhaust opening 110 with the air resistance as small as possible. The peripheral gas of the tornado type air flow formed within the chamber body is discharged through the air exhaust opening 110. The peripheral gas is not limited to be air, and it may contain small amount of the sample. An open oriented direction of the air exhaust opening is close to a direction reversing the velocity direction of the gas flow at the air exhaust opening.

The sampling device 100 may further include a filter screen located at first end side of the sample inlet and for preventing large particle substance from entering the sample inlet. The filter screen includes a rigid coarse strainer for filtration of large particles and a fine mesh strainer for filtration of fine particles.

The sampling device 100 may further include a temperature-controlling system adapted for controlling a temperature within the chamber body, and the temperature-controlling system includes a heater for rise of the temperature and a temperature sensor for measuring the temperature, provided within a wall of the chamber body. The sampling device 100 may further include a thermal insulation layer surrounding the wall of the chamber body. In this embodiment, the chamber body may be an integrated one, or may be an assembled one consisted of several components by means of welding, riveting, etc. The specific construction of the chamber body may not substantially effect on the air flow inside the chamber body.

The chamber body, in this embodiment, may be also provided with end cap 101, strainers 103, 104, inflation and exhaust air pumps 128, sample-supplying semi-permeable membrane 111, temperature controlling system, thermal insulation layer, etc., as those in the aforementioned embodiment. In this embodiment, the chamber body may further include a mixing region for mixing the carrier gas with the sample. That is, the mixing region is provided at a lower section of the chamber body is separated, e.g., by the semipermeable membrane 111, from a section of the chamber body where the tornado type air flow is formed. There may be two pieces of network metal 112, for clamping the semipermeable membrane 111 and protecting it from suffering an air impact.

The chamber body may include a carrier gas passage 121 at its lower part 113, which is provided for injection of the carrier gas which will be mixed with the sample in the funnel. The chamber body may further include a sample induction opening 120 at its lower part 113, through which the collected sample and the carrier gas are discharged after being mixed and preheated. Similarly, the bottom end face of the chamber body may be the same as that in the aforementioned embodiment, as shown in FIG. 4. The bottom end face of the chamber body may be provided with an inflator pump interface 122, an exhaust pump interface 123, a GC column/ion migration tube interface 124, a heating rod outgoing line 125, a temperature sensor outgoing line 126, a ventilation outlet 127 and a carrier gas tube interface 136. The inflator pump interface 122 and the exhaust pump interface 123 may be connected respectively with an air pump 128, for example, an inflator air pump and an exhaust air pump, for continuously supplying an air pressure so that a tornado type air flow is formed inside the sampling device 100, and, the flow speed of the exhaust pump is ten times or more than the inflator pump.

The exhaust pump interface 123 is arranged in a manner to make the air resistance as small as possible, so that the opening of the exhaust pump interface in the air guide chamber faces toward a gas flow on-coming direction, facilitating an easy inflow of the air flow into the exhaust pump interface. The exhaust pump interface 123 may not be connected to the air pump 128 and be served directly as the ventilation outlet. In order to discharge the tornado type suctioned and amplified gas flow, several ventilation outlets 127 may be formed. The GC column/ion migration tube interface 124 may be connected directly to the ion migration tube. The carrier gas tube interface 136 is connected to a molecular sieve 135 so that the carrier gas will be purified.

In another embodiment of the sampling device according to the disclosed technology, a section of the chamber body has an inner wall with a partially spherical shape, instead of a truncated conical shape. That is to say, the inner wall of this section of the chamber body is a cambered surface having a smaller diameter near the sample inlet side and a larger diameter near the sample outlet side, such that a tornado type air flow will be formed inside the chamber body.

In another embodiment of the detection apparatus 50 according to the disclosed technology, an example of the sample pre-processing device 200 included in the detection apparatus 50 is schematically shown in details in FIG. 5.

Referring to FIG. 5, the sample pre-processing device 200 includes a piston-type absorber 202, a piston cylinder 203, a thermal desorption chamber 204 and a pump 205. Structures and operations of these components will be described in detail hereafter.

The sampling device 100 is connected to and communicated with the piston cylinder 203 via a connection tube.

The connection tube may be provided therein with desiccants which can absorb moisture content and the like in the collected sample during the sample collection process, to protect the chromatographic column and migration tube of analytical device. The desiccants may be encapsulated in a desiccant bag, and a desiccant or desiccant bag fixation structure, e.g., a boss, may be provided in the connection tube, for preventing the desiccant or desiccant bag from moving under the action of the pump.

At least one portion of the connection tube, e.g., the portion coming after the desiccant, may be formed of flexible hose or bellows. During the sampling, such flexible hose or bellows is able to be prolonged or revolved so that orientation of the sample collection opening is adjustable, greatly easing collection of the sample. The distal end of the connection tube is configured to hermetically and detachably be connected to the piston cylinder 203.

Figure 6:
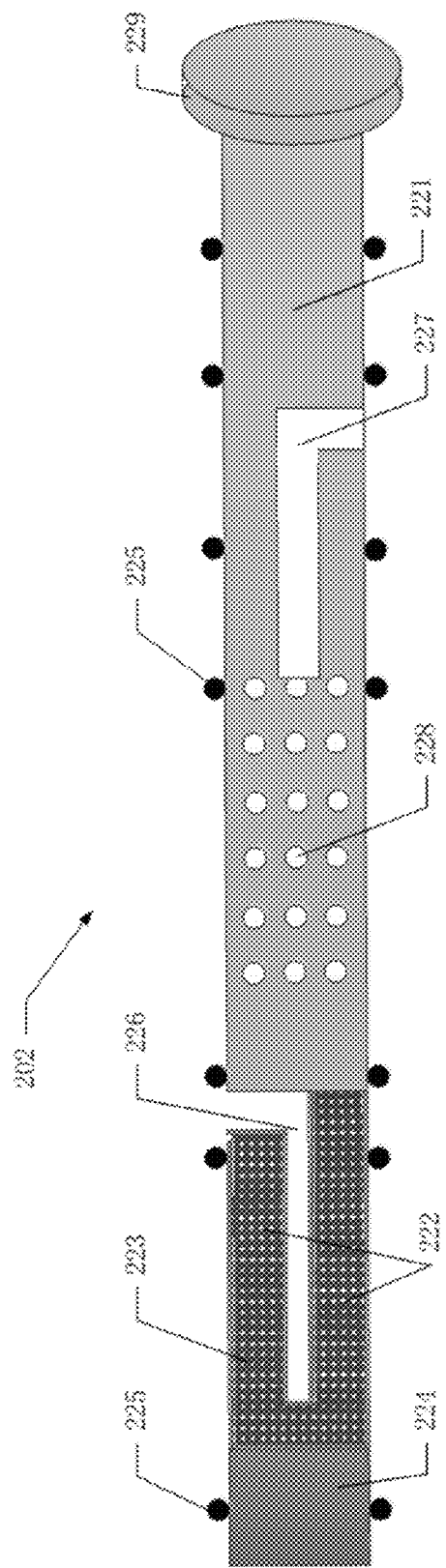
FIG. 6 is a schematic view of a piston-type absorber of a sample pre-processing device according to an embodiment of the disclosed technology.

FIG. 6 schematically shows an example of a piston-type absorber of a sample pre-processing device according to an embodiment of the disclosed technology. The piston-type absorber 202 is in a wholly cylindrical piston form and is able to reciprocate within the piston cylinder 203. The piston-type absorber 202 mainly includes a piston rod body 221 and an absorption cavity 222 connected to a distal end of the piston rod body 221. The piston rod body 221 may be made of heat resistant material having stable chemical property, for example, Teflon.

In an embodiment, the absorption cavity 222 has a net-like structure filled with adsorbents 223 therein, that is, net-like apertures are formed in wall of the cavity and the adsorbents are filled within the absorption cavity. Various kinds of the adsorbents with different absorption properties may be added selectively in accordance with different detection requirements. This selective addition of the adsorbents according to requirements enhances an adsorption selection to the sample to be detected, to a certain extent. A diameter of the filled adsorbent should be greater than size of the aperture of the net-like structure. Referring to FIG. 6, the absorption cavity 222 may be in a partial hollow form, that is, it may include an absorption passage 226 which has an L-shape or a crosier shape, with an opening formed on the wall of the cavity. As described hereafter, during the sampling, the absorption passage is in fluid communication with the sample collecting structure to receive the sample suctioned from the connection tube. By this way, not only the sample will go through the adsorbents, but also a contacting area between the sample and the adsorbents are greatly increased, facilitating adsorption of the sample.

In an example, the piston rod body 221 may include a cooling passage 227 and a plurality of through holes 228 formed on the lower part of the piston rod body. As described hereafter, the cooling passage 227 is configured to be communicated directly with ambient gas when the piston-type absorber is located in the sample collecting position, and to be communicated with ambient gas via cooling through hole formed on the piston cylinder when the piston-type absorber is located in the sample desorbing position. The cooling passage 227 may be in an L-shape or a crosier shape, with an opening to the ambient gas. The through holes 228 are configured to communicate the cooling passage 227 with the piston cylinder 203. This hollow piston rod body, on one hand, reduces a weight of the piston-type absorber, facilitating a quick rise and drop in temperature, and on the other hand, communicates the pump 205 with a cooling air inlet 23 (see FIG. 5 and FIG. 7) at an upper part of the piston cylinder 203 during desorption of the sample. The upper part of the absorber will be air cooled under the action of the pump, which accelerates the temperature dropping rate on the upper part of the piston-type absorber, facilitating a quick drop in temperature of the absorption cavity, as well as the adsorbents therein, at the lower part of the piston-type absorber. As a result, it is beneficial to the sample absorption.

In an embodiment, the piston-type absorber 202 may further include a thermal insulation pad 224 detachably connected to one end of the absorption cavity 222 away from the piston rod body 221. That is, the absorption cavity 222 is between the piston rod body 221 and the thermal insulation pad 224. In an embodiment, the adsorbents within the absorption cavity may be replaced when the piston-type absorber is pulled out or the piston cylinder is detached and the thermal insulation pad at the bottom of the absorber is unscrewed or removed. The thermal insulation pad may be made of Teflon. Provision of the thermal insulation pad reduces a thermal transmission from the thermal desorption chamber to the absorption cavity, which effectively ensures that the absorption cavity as well as the adsorbents is kept cool, for example., at an almost room temperature where the sampling or collection will be performed easily, when the piston-type absorber performs a sampling or collection.

Figure 7:
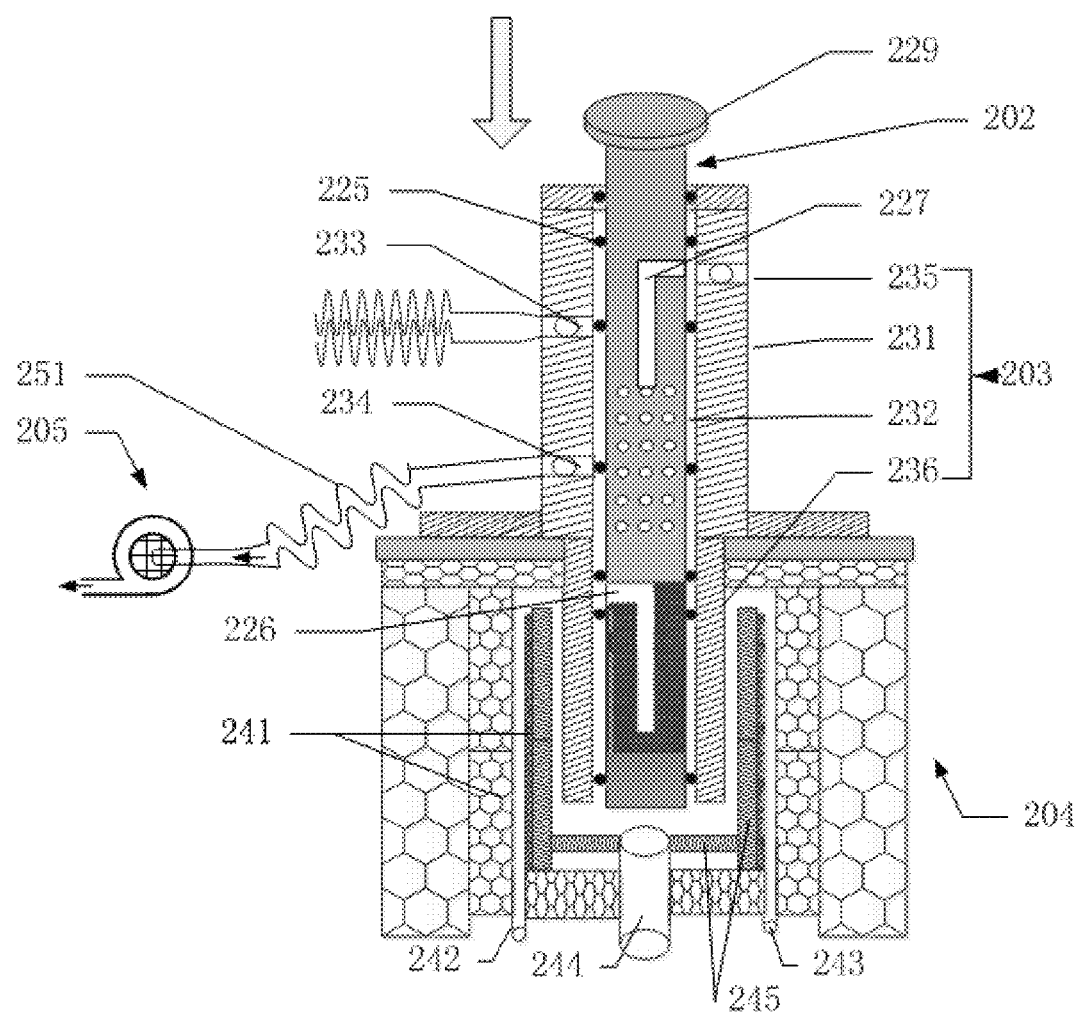
FIG. 7 is a schematic view of a sample pre-processing device according to an embodiment of the disclosed technology. The sample pre-processing device is in a sample desorbing state.

In an embodiment, the plurality of sealing rings 225 are sleeved on the piston-type absorber 202, e.g., around outer surface of the piston-type absorber 202, such that the piston-type absorber 202 are received hermetically within the piston cylinder 203. In an embodiment, the sealing rings 225 are configured such that the piston-type absorber 202 is kept in a sealed contact with inner wall of the piston cylinder 203 by the sealing rings 225 when it reciprocates between a highest position (for example, a sample collecting position) and a lowest position (for example, a sample desorbing position), in the piston cylinder 203, as shown in FIG. 5 and FIG. 7. In an embodiment, sealing rings 225 are provided at upper and lower positions adjacent to the opening of the absorption passage 226 and at upper and lower positions adjacent to the opening of the cooling passage 227, as shown in FIG. 6.

A push-pull handle 229 is provided at a distal end of the piston rod body 221 of the piston-type absorber 202 and is for reciprocating the piston-type absorber 202 within the piston cylinder 203 by means of user's pull and push operation.

Referring to FIG. 5 and FIG. 7, the piston cylinder 203 mainly includes a cylinder block 231, and a piston chamber 232 that is for accommodating the piston-type absorber 202 and is in fluid communication with the absorption cavity 222. The cylinder block 231 can be made of Teflon which has great strength, good heat resistance and stable chemical performance, and defines at least one section of the piston chamber 232. The cylinder block 231 is mounted on the thermal desorption chamber 204, and the cylinder block 231 is provided with a sampling connection gas nipple 233 being communicated with the piston chamber 232. As described above, distal end of the connection tube of the sampling device 100 is mounted or inserted hermetically and detachably to the sampling connection gas nipple 233 to achieve communication between a sample passage inside the sampling device 100 and the piston chamber 232. The sampling connection gas nipple 233 may be provided with an on-off valve for controlling this communication.

The cylinder block 231 may be further provided with a pump connection gas nipple 234 by which the pump 205 is in fluid communication with the piston chamber 232 through the conduit 251. In this way, during sampling, sample collection or sample pre-concentration, the pump 205, the conduct 251, the pump connection gas nipple 234, the piston chamber 232, the sampling connection gas nipple 233 and the connection tube sample collection opening constitute a connection path. With start-up of the pump 205, the sample to be sampled (for example, volatile substances, semi-volatile substances or surface contaminants) in the ambient gas is suctioned into the absorption cavity 222, and is absorbed and pre-concentrated by the absorption cavity 222. During the sampling, the pump 205 operates constantly to collect and pre-concentrate the sample within the absorption cavity. During the sampling process, the whole piston-type absorber is at room temperature.

The piston cylinder 203 may further include a guide rail 236 provided in the thermal desorption chamber 204 for guiding movement of the piston-type absorber 202 in the thermal desorption chamber 202, which effectively prevents shaking of the piston-type absorber 202 and thus enhances the degree of firmness. The guide rail 236 is connected to the cylinder body 231 and defines a section of the piston chamber 232.

As shown in FIG. 5 and FIG. 7, thermal desorption chamber 204 mainly includes a chamber body 241, and an interior space defined by the chamber body 241 adapted for performing a thermal desorption therein. The chamber body 241 is formed with a carrier gas inlet 242, a shunting and/or sweeping gas outlet 243, and an interface 244 for connection to an analytical instrument such as chromatographic column, IMS.

In the chamber body of the thermal desorption chamber 204, a liner 245 having a stable chemical property may be embedded hermetically. The liner 245 may effectively prevent direct contact between the sample and metallic wall of the thermal desorption chamber. The liner 245 may be replaced regularly, which avoids direct pollution of the sample to the thermal desorption chamber, reduces a sampling distortion rate, and enhances accuracy and reliability of sample detection. An outer wall of the chamber body of the thermal desorption chamber 204 may be provided/covered with a heating structure or a heating film, for heating the thermal desorption chamber 204. The thermal desorption chamber 204 may be provided with a temperature sensor, for example on the outer surface of the chamber body, for real time detecting and monitoring of temperature within the thermal desorption chamber. In addition, the outer wall of the chamber body of the thermal desorption chamber 204 may be covered with a thermal insulation cotton for thermally insulating the thermal desorption chamber, so as to save the power consumption. The heating structure, the temperature sensor and/or the thermal insulation cotton are components, of the thermal desorption temperature controlling system, which keep the temperature of the thermal desorption chamber at a constant temperature, e.g., 80° C.-300° C., under the control of a controller. The thermal desorption chamber may adopt a programmed heating mode, which reduces the power consumption.

A thermal insulation structure such as a porous ceramic thermal insulation disc, may be provided or inserted between the thermal desorption chamber 204 and the piston cylinder 203, which will effectively insulate heat exchange between the thermal desorption chamber 204 and the upper part of the piston-type absorber (e.g., the piston rod body) during the desorption of the sample, and will effectively insulate heat exchange between the thermal desorption chamber and the piston-type absorber and a heat exchange between the thermal desorption chamber and the upper part of the piston cylinder during the collection of the sample. This ensures the whole piston-type absorber is at the room temperature during the collection of the sample, facilitating collection of the sample.

When it is time to desorb the sample, the thermal desorption temperature controlling system is operated first to maintain the temperature in the thermal desorption chamber at a suitably constant high temperature (80° C.~300° C.). The piston-type absorber with the suctioned sample is pushed quickly into the thermal desorption chamber at the high temperature. The adsorbents into the thermal desorption chamber are heated rapidly so that the sample suctioned in the absorption cavity will be thermal desorbed at the high temperature. The desorbed sample will be mixed with pre-heated carrier gas from thermal desorption chamber through the carrier gas inlet, and finally taken by the carrier gas into the detection device or the analytical instrument for detection or analysis.

As described above, the pump 205, the piston chamber 232, the plurality of through holes 228 formed in the piston rod body, the cooling passage 227, and the cooling air inlet 235 formed on the piston cylinder 203 constitute a communication path while the absorption cavity is pushed into the thermal desorption chamber. The upper part (including the piston rod body) of the piston-type absorber outside the thermal desorption chamber may be air cooled by the air exhaust operation of the pump 205, which facilitates a next adsorption and collection or pre-concentration of the sample.

This sample pre-processing device having the collection or pre-concentration function may be used directly as IMS instrument or GC, or be served as a sample-supplier of trace chemical substance analytical instruments including IMS-GC, GC-MS, etc.

Operations of the abovementioned sample pre-processing device will be described with reference to FIG. 5 and FIG. 7.

First, the piston-type absorber 202 is pulled to the sample collecting position as shown in FIG. 5, such that the absorption cavity 222 is in fluid communication with the sampling device 100. Here, the pump 205, the conduit 251, the pump connection gas nipple 234, a section of the piston chamber 232 (including the section enclosing the absorption cavity), the sampling connection gas nipple 233, the connection tube and the sample collection opening 124 constitute a communication path by means of the sealing rings 225. Then, the pump 205 is started up, so that a sample (for example, volatile substances, semi-volatile substances or surface contaminants) in the ambient gas is suctioned into the absorption cavity 222, and is absorbed and pre-concentrated by the absorption cavity 222. During sampling, the pump 205 operates constantly to collect and pre-concentrate the sample within the absorption cavity. During the sampling process, the whole piston-type absorber is at room temperature.

Next, the thermal desorption temperature controlling system is started up, so that the temperature of the thermal desorption chamber 204 is kept at a constant high temperature. Then, the piston-type absorber 202 is moved rapidly to be positioned at the sample desorbing position as shown in FIG. 7, so that the absorption cavity 222 is positioned within the thermal desorption chamber 204. The absorption cavity 222 may be sealed by the sealing rings 225 into the lower part of the piston chamber 232, so that it is sealed within the thermal desorption chamber 204. Here, the adsorbents that are pushed into the thermal desorption chamber 204 are heated up rapidly so that the sample absorbed in the absorption cavity 222 is desorbed instantly at high temperature. The desorbed sample is mixed with a pre-heated carrier gas inducted from the carrier gas inlet 242 of the thermal desorption chamber 204. Finally, it is brought by the carrier gas into a detection device or analytical instrument (not shown), for detection or analysis.

During the desorption of the sample within the thermal desorption chamber, the pump 205, the conduit 251, the pump connection gas nipple 234, a section of the piston chamber 232 (namely the section outside the thermal desorption chamber 204), the plurality of through holes 228 formed in the piston rod body 221, the cooling passage 227, and the cooling air inlet 235 in the piston cylinder 203 constitute a path or space that is in fluid communication with ambient gas. According, the upper half part of the piston-type absorber 202 outside the thermal desorption chamber 204 may be air-cooled by the suction function of the pump, so that temperature of the part of the piston-type absorber positioned outside the thermal desorption chamber is maintained at room temperature, facilitating a next adsorption and collection or pre-concentration of the sample Referring to FIG. 8, a sample pre-processing device 300 of another embodiment of the detection apparatus 50 is shown. The sample pre-processing device 300 includes a gas suction pump 320, an absorber 330, a piston cylinder block 340 and a desorption cylinder block 350. The desorption cylinder block 350 defines a desorption chamber 356. The desorption cylinder block 350 is provided with an analyzer interface 352 that is communicated (in fluid communication) with the desorption chamber 356, a carrier gas inlet 351 and a carrier gas sweeping/shunting interface 353. An outer wall of the desorption cylinder block 350 is provided with a heating film and a temperature sensor (not shown). The analyzer interface connects with the chromatographic column, IMS, MS, DMS and the like. The carrier gas inlet is connected to a carrier gas supplier for obtaining the carrier gas. The heating film heats the thermal desorption chamber 356. The temperature sensor is for real-time reading temperature of the desorption chamber and is connected to external temperature-controlling circuit, for achieving temperatur control. The piston cylinder block 340 is provided with two piston chambers 341 each of which is mounted with one absorber 330. The piston cylinder block 340 is mounted on the desorption cylinder block 350, and the two piston chambers 341 are in fluid communication with the desorption chamber 356. The lower part of the piston cylinder block 340 is inserted into the desorption chamber 356, and, an opening is formed at the front of the piston chamber 341, for connection to the desorption chamber 356. The piston cylinder block 340 is provided with a sample gas inlet port 342 and a gas suction pump port 343, and, the sample gas inlet port 342 is connected to the sampling device 100 via bellows tube 312, while the gas suction pump port 343 is connected to the gas suction pump 320. The absorber 330 includes an adsorption riddle drum 332 and a piston rod 331 connected with each other. The adsorption riddle drum 332 is a drum having pores on its side wall, and the adsorption riddle drum 332 is for storage of the adsorbents. The absorber 330 has a cylindrical piston structure which may carry out a reciprocating movement. The piston rod 331 is slidably mounted within the piston chamber 341 and drives the adsorption riddle drum 332 to slide along the piston chamber 341. The piston rod 331 is able to be inserted into the desorption chamber 356, and, the adsorption riddle drum 332 is able to be in fluid communication with both the sample gas inlet port 342 and the gas suction pump port 343 simultaneously. In order to facilitate pull and push of the piston rod 331, a piston handle 371 is provided on rear end of the piston rod.

When in use, adsorbents are placed within the adsorption riddle drum 332. Firstly, the absorber 330 is pulled up so that the adsorption riddle drum 332 is in fluid communication with the sampling device 100 and the gas suction pump 320. When the gas suction pump 320 implements a suction operation, the sampling device 100 suctions the sample gas. The sample gas goes through the adsorption riddle drum 332 and the sample contained in the sample gas is absorbed by the adsorbents. After the sample is richly collected by the adsorbents, the absorber 330 is pushed down into the preheated desorption chamber 356, for desorption of the sample. The desorbed sample is mixed with preheated carrier gas from thermal desorption chamber through the carrier gas inlet, and finally goes through the analyzer interface 352 into GC-IMS, IMS, GC-MS, GC-DMS or other analytical instrument for detection. Two absorbers 330 may be used alternately in the embodiment of the disclosed technology, that is, one is pulled out for sampling (of a latter sample) while the other one is pushed down for analysis and detection (of a previous sample). Accordingly, the sampling device will absorb the sample rapidly in full time, and reflects the obvious superiority in detection, especially during processing of a plurality of samples to be detected. The absorber may implement a concentration on the sample, enhancing accuracy of detection of the analytical instrument.

In an embodiment, the adsorption riddle drum 332 is formed with an adsorption screen opening 372 that is able to be in fluid communication with the sample gas inlet port 342. Through the adsorption screen opening 372, the inducted sample gas goes rapidly into the adsorption riddle drum 332 having a structure that effectively enlarges an absorption area per unit time and increases speed of the sample collection. In an embodiment, the sample gas inlet port 342 and the gas suction pump port 343 are arranged along an axial direction of the piston chamber341, and a distance between the sample gas inlet port 342 and the gas suction pump port 343 is slightly less than a length of the adsorption riddle drum 332 so that the adsorption screen opening 372 is just matched and in fluid communication with the sample gas inlet port 342. Moreover, the adsorbents in the adsorption riddle drum 332 may be replaced when the thermal insulation pad 333 positioned over a top end of the absorber is unscrewed. Any types of the adsorbents will be used relying on the demands.

In an embodiment, the outer wall of the desorption cylinder block 350 is further provided with a temperature sensor (not shown) and a thermal insulation layer 354. The temperature sensor senses temperature of the desorption cylinder block, and is connected to a controller which controls the temperature of the desorption chamber 356 in a programmed heating manner, effectively reducing power consumption. A thermal insulation cotton is served as the thermal insulation layer 351, for thermally insulating the desorption cylinder block, to reduce power consumption. The desorption cylinder block 350 is provided with a carrier gas sweeping/shunting outlet 353 that is communicated to the desorption chamber 356. If the mixed sample gas fails to completely go through the analyzer interface 352, it is discharged through the carrier gas sweeping/shunting outlet. A thermal insulation disc 360 for effectively cutting off a thermal transmission between the desorption cylinder block 350 and the piston cylinder block 340 is provided between the piston cylinder block 340 and the desorption cylinder block 350. The piston cylinder block 340 is connected to the desorption cylinder block 350 and the thermal insulation disc 360 through a thread sealing manner. The thermal insulation disc 360 is made of porous ceramic material.

In order to obtain a dried sample gas, a desiccant bag 313 for eliminating water vapor in the mixed gas is disposed in the bellows tube 312, to protect the chromatographic column and the detection device. The desiccant bag 313 is fixedly mounted in a groove 314 of the bellows tube 312. The sampling device 310 has trumpet-shaped suction head provided with a micro strainer 315. Provision of the micro strainer 315 prevents large particle substance from entering and blocking the path.

In an embodiment, each of the piston chambers 341 is formed with a cooling air port 344 with an inlet valve 374. The piston rod 331 is formed with a cooling cavity 334 that is able to be in fluid communication with the cooling air port 344, and, a side wall of the piston rod 331 is opened with a plurality of ventilation holes 373 that are communicated to the cooling cavity 334 and at least some of which are able to be in fluid communication with the gas suction pump port. If it is required to cool down the absorber 330, the absorber 330 is pulled out so that the cooling cavity 334 is in fluid communication with the cooling air port 344 and the inlet valve 374 is turned on, then a cooling air, under the action of the gas suction pump, flows from the cooling air port 344, to cooling down the piston rod 331 and the adsorption riddle drum 332.

In an embodiment, a plurality of O-type sealing rings 335 are provided between the absorber 330 and the piston chamber 341.

In an embodiment, a liner 355 is provided at the inner wall of the desorption cylinder block 350. The desorption cylinder block 350 may be made of stainless steel and is embedded hermetically with the liner 355 made of PTFE material having stable chemical performance. The liner 355 may be replaced regularly, which, on one hand, keeps the sample gas from being in contact with/reacting with metal material, thereby avoiding distortions of the sample to be detected and its detection signal; on the other hand, prevents the large particle substance falling into and block the chromatographic column.

In an embodiment, a thermal insulation pad 333, for thermally insulating heat from the desorption chamber 356, is provided at a bottom of the adsorption riddle drum 332, preventing the heat in the desorption chamber 356 from being transferred to the adsorption riddle drum 332. In an embodiment, the bottom of the adsorption riddle drum 332 is open, and the thermal insulation pad 333 is connected to adsorption riddle drum 332. The adsorbents may be replaced when the absorber 330 is pulled out or the piston cylinder block 340 is detached and the thermal insulation pad at the bottom of the absorber 330 is unscrewed. Any types of the adsorbents will be used relying on different detection purposes (a diameter of the filled adsorbent should be greater than aperture/mesh size of the adsorption riddle drum 332), which greatly enhances flexibility of the apparatus. The thermal insulation pad may be made of PTFE material having good thermal insulation performance. The thermal insulation pad ensures that the adsorption riddle drum 332 and the adsorbents are near room temperature during the sample collection of the absorber 330, which facilitates adsorption and collection of the sample.

In an embodiment, the piston rod 331 and adsorption riddle drum 332 in the absorber 330 of an embodiment of the disclosed technology are formed integrally and are made of heat resistant material having stable chemical properties, such as PTFE. The piston cylinder block 340 may be made of PTFE material having great strength, good heat-resistance performance and stable chemical performance. In order that the absorber 330 may be moved stably along the piston chamber341, a sealed guide rail, for providing support and seal of the conduits during sampling, collection, cooling and thermal desorption, may be arranged in the piston chamber 341.

Referring to FIG. 8, for convenience purposes, in this figure, the left one of the two absorbers is named as first absorber while the right one is named as second absorber. When sampling will be performed to an article to be inspected, first, the heating film at the outer wall of the desorption cylinder block is enabled upon setting a temperature. After the temperature is stable, the two absorbers are pushed down into the desorption chamber to purify the adsorbents. Then, the two absorbers are respectively pulled up so that the first absorber is moved to a position at which the left absorber in FIG. 8 is located while the second absorber is moved to a position where the upper end of the adsorption riddle drum is slightly lower than the sample gas inlet port at the upper end of the piston cylinder block (not to form a suction path, but to help cool the absorber for subsequent adsorption of the sample). The power of the gas suction pump for sampling is switched on, and, the trumpet-shaped suction head of the sampling device is aimed to the article to be inspected at short range. Under the action of the gas suction pump, volatile gas from the article to be inspected is collected for 3-5 minutes, for collection of the sample. After sample collection, the adsorption riddle drum in the first absorber is pushed down completely into the desorption chamber, for desorption of the sample, meanwhile the second absorber is pulled up to a position where the sample gas inlet port, the adsorption riddle drum and the gas suction pump port constitute a fluid communication path. With repetitive operations of the above, a full-time rapid adsorption, collection and desorption of the sample of a plurality of articles to be inspected will be achieved. The desorbed sample is mixed evenly with the carrier gas from the carrier gas inlet and then is inducted to a sample exhaust port that is connected to the detection apparatus 50 or a separate apparatus, so that desorption and sampling of the sample will be achieved.

FIG. 9 is an overall structural schematic view of an embodiment of a sample analyzing device 400 in a detection apparatus 50 according to the disclosed technology. The sample analyzing device 400 may generally include a sample leading-in unit and an IMS unit.

The sample leading-in unit includes: a MCC. In some embodiments, the MCC 401 may be formed by clustering the plurality of independent capillary columns in parallel into a bundle. In some embodiments, the MCC 401 may be formed by defining a plurality of capillary pores in parallel in one column. In some embodiments, the MCC 401 may be formed of non-metallic material. For example, generally, the capillary columns may be formed of glass material. The capillary columns may be also formed of other materials. The MCC 401 is configured to have an inlet end and an outlet end substantially flush with each other. A MCC 401 consists of hundreds of capillary columns in parallel. For example, 500~5000 capillary columns, each having an inner diameter of 20~100 μm, for example ~40 μm, in parallel are clustered within a glass column having the cross-section of regular hexagon. Each of the capillary columns may be coated with a layer of stationary material/phase on its inner surface. The stationary material/phase used depends on usage and demands. Due to its great separation ability, the MCC 401 is generally in a form of pen-shaped column having relatively smaller size in length (of 40~250 mm), to meet the separation demand. Columns having relatively greater size in length may be coiled into a disc shape. By their interactions with the stationary phases of the capillary columns for different retention times, components of the mixed sample are separated from one another. Retention times for these capillary columns are in order of magnitude of seconds to minutes (generally tens of seconds to several minutes, the minimum peak width is several seconds).

The structure of the MCC 401 has the following advantages. First, thousands of capillary columns are clustered so that the MCC 401 has greater capacity, and greater sensibility. Second, the capillary column in the MCC 401 is much finer in diameter, for example, the inner diameter of the capillary column may be 20~100 μm, while conventional capillary column has an inner diameter of 0.25-0.53 mm, that is, these capillary columns in the MCC 401 have greater separation effect since the smaller in size in length of the capillary columns may achieve a greater separation effect. Third, the pen-shaped capillary columns 401 (of 40-250 mm) in the bundle have less pressure gradients than conventional capillary columns (generally of 40-250 mm), so the flow velocity through the capillary columns 401 of the bundle is greater by 2-3 orders of magnitude than that through the conventional capillary columns, and may be in a greater flow-rate range (of 20-150 ml/min). Therefore, the MCC 401 enables not only fast separation but also isothermal separation. With the above advantages, the MCC 401-IMS apparatus may obtain approximately real-time separation and detection. The smaller size in length of the MCC 401 helps to achieve a portable MCC-IMS apparatus In order protect the glass column and enhance the strength of the MCC to prevent accidental damage, the sample leading-in unit includes a metallic sleeve 420 that encloses and protects the MCC 401. FIG. 9 is a situation in which one metallic sleeve 420 is coupled around a regular hexagonal glass column, that is, the pen-shaped glass MCC 401 has a cross-section of regular hexagon. The MCC 401 may have a cross-section of any other shape, such as circular.

The sample leading-in unit further includes a temperature controlling system which is in combination with the MCC 401 to control the temperature of the MCC 401.

Specifically, the temperature controlling system of the sample leading-in unit includes a thermal conductor 402 configured to be in a direct contact with the metallic sleeve 420 by which the MCC 401 is enclosed. The temperature controlling system further includes at least one heater 404 and at least one sensor 405 embedded within the thermal conductor 402. Cooperation of the at least one heater 404 and the at least one sensor 405 may achieve the control on temperature of the thermal conductor 402. Various types of the heater may be used. For example, a plurality of hearing rods 404, i.e., one or more heating rods 404, e.g., 2, 3, 4, 5, 6, 7, 8, 9, 10 heating rods 404, may be embedded in the thermal conductor 402. The plurality of hearing rods 404 may be distributed uniformly in the thermal conductor 402, enhancing rapidly and evenly the temperature of the thermal conductor 402. FIG. 9 shows a situation in which one heating rod is used. The thermal conductor 402 may be embedded therein with hot filaments that are arranged to facilitate the uniform heating. For example, the thermal conductor 402 itself may be a kind of heating element that can be heat up.

In some embodiments, the sensor 405 may be provided adjacent to the metallic sleeve 420, so that the temperature measured by the sensor 405 is very close to the temperature within the capillary columns. A plurality of sensors 405 may be distributed uniformly around the thermal conductor 402 adjacent to the metallic sleeve 420.

Figure 10:
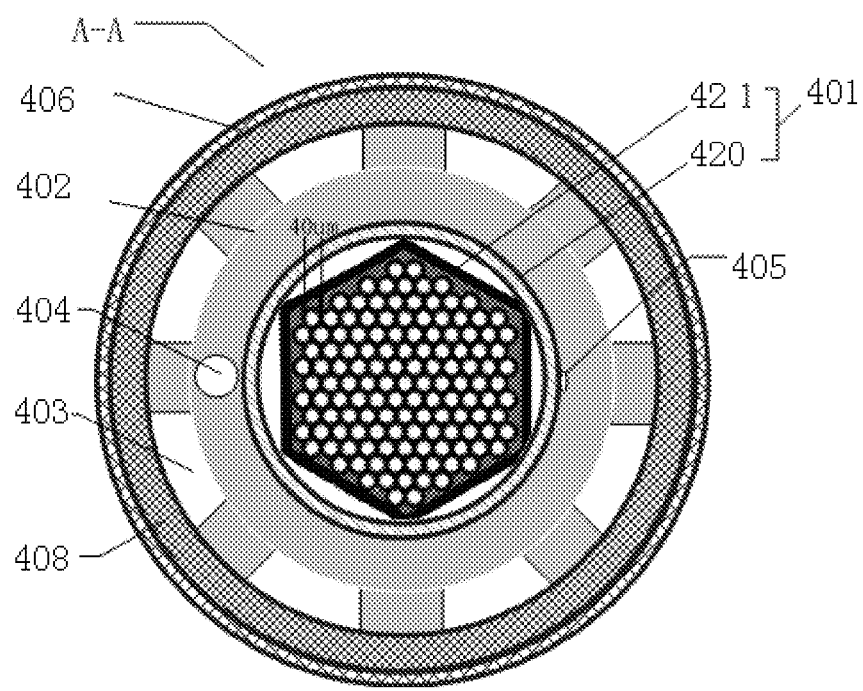
FIG. 10 is a sectional view of a sample analyzing device according to an embodiment of the disclosed technology along a line A-A.

In some embodiments, the thermal conductor 402 includes a plurality of protrusions 430 on a periphery of the thermal conductor 402, where spaces 403 are defined among the plurality of protrusions 430. These spaces may be served as grooves 403, or as a fluid passage 403 through which a fluid passes, as shown in FIG. 10.

Sizes of these protrusions 430 may be the same or different. The spacing between every two of the protrusions 430 may be the same or different. For example, some of the protrusions 430 have relative greater size while the rest of the protrusions 430 have relative smaller size. For example, if two columns of protrusions 430 are served as a group, the spacing between every two of the groups of protrusions 430 is greater than that between two columns of protrusions 430 in every group. Also, the protrusions 430 may be arranged non-uniformly. It should be understood for those skilled in the art that the protrusions 430 may have other sizes and spacings, and also may be arranged in other manners.

In other words, the thermal conductor 402 may include two portions; one is a base of the thermal conductor 402 while the other one is a protrusion 430 of the thermal conductor 402. In some embodiments, the base has a relatively smaller radial thickness, and the protrusion 430 has a relatively greater height. Provision of the plurality of protrusions 430 on the thermal conductor 402 helps the fluid to flow among the protrusions 430, so as to exchange heat with the thermal conductor 402. In some embodiments, for example, the inducted gas flows among the plurality of protrusions 430, accelerating thermal exchange between the plurality of protrusions 430 on the thermal conductor 402 and the inducted gas. Here, the plurality of protrusions 430 can serve as heat sink. In some embodiments, conduits through which the fluid passes may be wound around the plurality of protrusions 430. By the heat exchange between high-temperature fluid or low-temperature fluid within the conduits and the thermal conductor 402, temperature of the thermal conductor 402 is controllable.

In some embodiments, the base of the thermal conductor 402 has a relatively smaller thickness, and a heating film is disposed among the plurality of protrusions 430 such that the thermal conductor 402 may be heated. Meanwhile, conduits of heat medium fluid are provided among the plurality of protrusions 430, achieving a drop in temperature of the thermal conductor 402 via the thermal transmission. With this arrangement together with the sensors 405, temperature of the thermal conductor 402 may be controlled rapidly.

Figure 12:
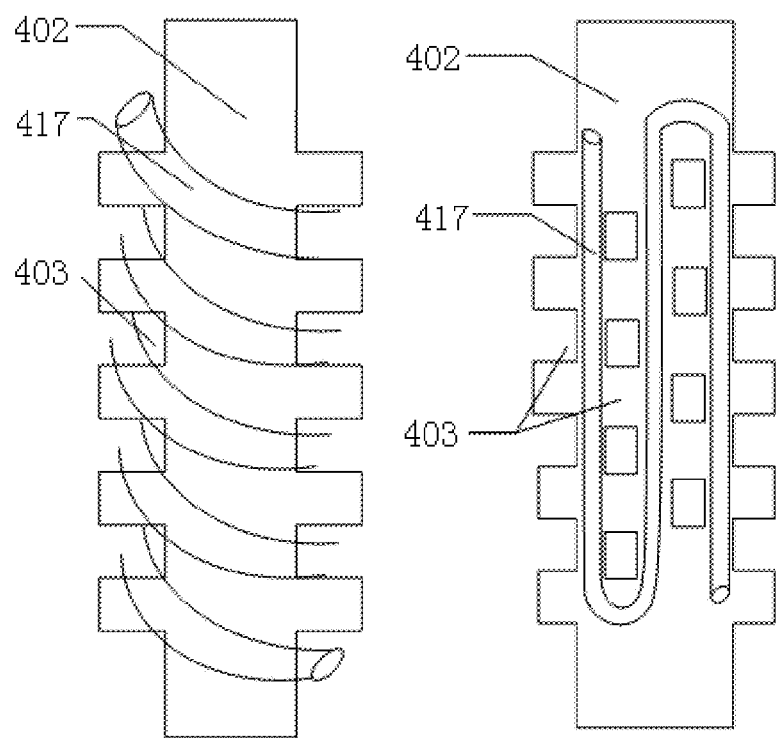
FIG. 12 is a sample analyzing device according to an embodiment of the disclosed technology, on which a plurality of protrusions on a thermal conductor and an arrangement of fluid conduits among the plurality of protrusions are provided.

Provision of the plurality of protrusions 430 may be regarded as that the thermal conductor 402 has trenches where heat medium fluids or heat medium fluid conduits are received, for thermal transmission. Specifically, FIG. 12 shows a situation where fluid conduits are wound among the plurality of protrusions 430. The heat medium fluid conduits may be wriggly go through the plurality of protrusions 430, or the heat medium fluid conduits are spirally around the thermal conductor 402 among the plurality of protrusions 430 of the thermal conductor 402, so that a thermal transmission is implemented between the heat medium fluid conduits and the thermal conductor 402. It should be understood that, the fluid conduits may be arranged in the passages or trenches constructed by the plurality of protrusions 430 in any manner, here, the protrusions 430 not only are used to implement a thermal transmission with the heat medium fluid conduits, but also act to support the conduits.

In some embodiments, the plurality of protrusions 430 may be regarded as thermal dissipation protrusions 430, as heat is taken away directly by fluids. The plurality of protrusions 430 may define fluid passages among the plurality of protrusions and for fixation of the fluid passages.

In another embodiment of the disclosed technology, the sample leading-in unit may further include a housing 406 enclosing the temperature controlling system. In some embodiments, the sample leading-in unit may further include a thermal insulation layer 408 disposed between the housing 406 and the thermal conductor 402. In some embodiments, the housing 406 may be enclosed around outer surface of the thermal conductor 402 in a sealing manner. When the thermal conductor 402 is enclosed by the thermal insulation layer 408 and the housing 406, the plurality of protrusions on the thermal conductor 402 may be used to support the thermal insulation layer 408 and the housing 406. As shown in FIG. 9, a plurality of passages is formed between the plurality of protrusions and the thermal insulation layer 408. Heat medium fluid conduits may be arranged at the periphery of the thermal conductor 402 by passing through these passages or the abovementioned trenches, for sufficiently thermal transmission.

In some embodiments, air pump 418 may be provided to connect the abovementioned trenches 403 through conduits 417. Through the conduits 417, the pressured gas is conducted by the air pump 418 into the trenches 403 among the plurality of protrusions 430, facilitating cooling or heating up of the thermal conductor 402. In some embodiments, fluids are introduced directly into the trenches formed among the plurality of protrusions 430, for thermal transmission.

In some embodiments, the inlet end of the MCC 401 goes beyond the housing 406 of the sample leading-in unit. A portion of the metallic sleeve 420, along with the MCC 401, also goes beyond the housing 406.

Since a flow velocity of the sample in the MCC 401 is greater than that in conventional gas chromatographic column, interfaces of the sample leading-in unit and the IMS unit are particularly important. The interfaces of the sample leading-in unit and the IMS unit are particularly important functioned to introduce the sample separated rapidly from the MCC 401 smoothly without any quality degradation into the reaction region of the IMS unit.

In some embodiments, the sample analyzing device 400 further includes a thermal insulation positioning unit 411 configured for connection of the sample leading-in unit and the IMS unit therebetween, and for cutting off a thermal transmission between the sample leading-in unit and the IMS unit, so that the sample leading-in unit and the IMS unit are independently controlled respectively in temperature.

Figure 11:
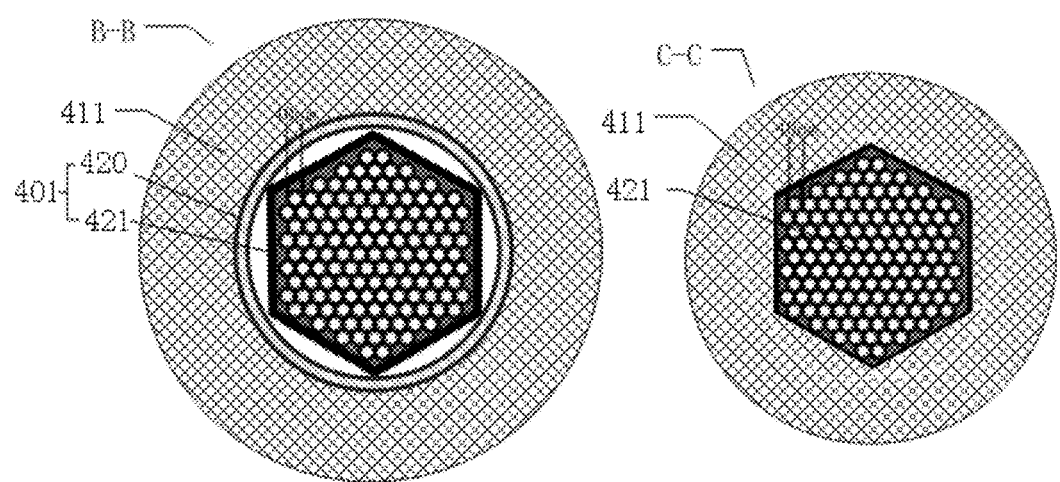
FIG. 11 is a sectional view of a sample analyzing device according to an embodiment of the disclosed technology along a line B-B and a line C-C.

In some embodiments, the thermal insulation positioning unit 411 includes a first connection end connected to the outlet end of the sample leading-in unit, and a second connection end connected to the IMS unit. Specifically, the first connection end is connected to and sealed up at one end of the MCC. The second connection end has a shape that complements a shape of the opening of the cavity of the ion mobility analysis unit. Shape of the thermal insulation positioning unit 411 is shown in the cross-sectional views of FIG. 9 and FIG. 11. The thermal insulation positioning unit 411 has a stepladder shape of cross section, and, FIG. 11 shows the cross-sectional views along line B-B and line C-C, respectively. In some embodiments, a gasket may be provided on an outer surface of a section of the thermal insulation positioning unit 411. The gasket 413 may act as a sealing function. When the sample leading-in unit is inserted into the IMS unit, the thermal insulation positioning unit 411 is connected therebetween. Here, a good seal is necessary to avoid leakage of the particles within the reaction region 414 or to prevent ambient gas from entering the reaction region 414 to adversely affect accuracy of the measurement.

The thermal insulation positioning unit 411 may be made of plastic material, for example, PEEK or Teflon. The thermal insulation positioning unit 411 may be made of other non-metallic materials having high temperature resistance performance and thermal insulation performance. For example, it may be made of materials including refractory material, asbestos, etc. With the thermal insulation positioning unit 411, the outlet end of the MCC 401 made of non-metallic material is inserted directly into the cavity of the IMS unit, namely, into the reaction region 414 of the IMS unit, through the sample leading-in opening of the IMS unit. Meanwhile, the metallic sleeve 420 is prevented from being close to the ion region of the IMS unit, avoiding interference of the metallic sleeve 420 to accuracy of the IMS unit. Specifically, the metallic sleeve 420 is kept out of the sample leading-in opening of the IMS unit. In an embodiment, the metallic sleeve 420 is kept away from the sample leading-in opening of the IMS unit.

With this arrangement, the sample is transmitted into the reaction region 414 of the IMS unit, avoiding a problem that gaseous material inducted into the ionization region 415 is hit, for example, by high-energy ray beams, into ion fragments. Meanwhile, the gaseous material may be separated from each other by the capillary columns, to meet analytical requirements, and is transmitted into the reaction region 414 for analysis.

In some embodiments, the thermal insulation positioning unit 411 may be integrated with the sample leading-in unit. In this case, one end of the sample leading-in unit may be sealed up by the thermal insulation positioning unit 411, while the outlet end of the sample leading-in unit may run out of the thermal insulation positioning unit 411, as shown in FIG. 9. Here, the outlet end of the sample leading-in unit including the thermal insulation positioning unit 411 is configured as shown in FIG. 9. That is, the MCC 401 is enwrapped by the end of the thermal insulation positioning unit 411, and, a part of the MCC is directly enwrapped by the non-metallic material of the thermal insulation positioning unit 411.

Arrangement of the thermal insulation positioning unit 411 enables a convenient and direct insertion of the sample leading-in unit into the cavity, namely the reaction region 414, of the IMS unit. It is especially important in a situation where a rapid analysis of the gas sample is required. The sample leading-in unit may be temperature-controlled independently. The temperature of the sample leading-in unit may be controlled independently in a preparation time. When the sample leading-in unit is in a desired temperature condition, the sample leading-in unit is inserted into the IMS unit. Connection and relative position between the sample leading-in unit and the IMS unit are achieved by use of the thermal insulation positioning unit 411. Due to thermal insulation property and rigidity of the thermal insulation positioning unit 411, accuracy of the measurement of the IMS unit will not affected by the temperature of the sample leading-in unit, and a positional relationship between the sample leading-in unit and the IMS unit may be determined and controlled. With this arrangement, connection and disconnection between the sample leading-in unit and the IMS unit may be implemented conveniently. It has a positive significance in the practical inspection process, greatly facilitates inspections on different samples, ease of transportation, and, achieves a reduced volume of the whole system. For example, a plurality of sample leading-in units may be equipped, which facilitates inspections on different samples and increases inspection speed and accuracy.

In some embodiments, a length of the metallic sleeve 420 of the MCC 401 is configured so that the metallic sleeve 420 does not get into the ionization region 415 of the IMS unit when the MCC 401 is inserted into the cavity 414 of the MCC. The end of the metallic sleeve 420 is terminated in the thermal insulation positioning unit 411, for example, at a position shown in FIG. 9. However, it should be noted that location of the metallic sleeve 420 is variable as long as the metallic sleeve 420 is kept out of the reaction region 414 where the ions are contained. For example, the metallic sleeve 420 is kept out of, or is kept away from the sample leading-in opening of the IMS unit.

In some embodiments, the sample analyzing device 400 further includes an IMS unit adapted for analyzing a sample led in by the sample leading-in unit. The IMS unit includes a cavity 414 for gas reaction, and the cavity 414 has a sample leading-in opening for leading-in of the sample. The IMS unit further includes an ionization region 415.

Referring to FIG. 9, the sample leading-in unit is positioned at an upper side of the IMS unit, and, the ionization region 415 is positioned at a lower side. In some embodiments, it is advantageous to arrange the sample leading-in unit with relative to the ionization region 415 of the IMS unit. Different from the prior art technical concept that the sample is ionized after being inducted into the ionization region 415, the sample leading-in unit of the disclosed technology is configured to keep the sample to be analyzed away from the ionization region 415 but to directly induct the sample to be analyzed into the reaction region 414. It advantageously prevents generation of molecular ion fragments, and avoids a problem in the prior art that the sample inducted into the ionization region 415 is hit into ion fragments, e.g., due to turbulence caused by non-linear gas passage. That is, the sample is inducted smoothly into the IMS unit while being separated rapidly.

In some embodiments, the IMS unit 412 is dual mode (i.e. at the same time has positive mode migration tube and negative mode migration tube respectively analyses cation and anion), the reaction region 414 is between the positive mode migration tube 422 and the negative mode migration tube 423, and, the ionization region 415 and the reaction region 414 are arranged independently and are connected via an opening that can be closed and opened, as the arrangement shown in FIG. 9. For example, the ionization region 415 is adjacent to the reaction region 414 side.

In some embodiments, carrier gas 416 such as air is inducted into the ionization region 415, and is ionized in ionization region 415 to generate electrically charged carried gas, for example, $H^+(H_2O)_n$ and $O_2^-(H_2O)_n$. The electrically charged carried gas is transmitted into the reaction region and is reacted with the sample therein, so that the sample molecules are with positively or negatively. It is different from the prior art that the sample gas is ionized together with the carrier gas. For example, bio-macromolecule is combined with hydrated proton or hydrated oxygen ion to form molecule with positively or negatively, instead of being ionized into molecular fragment. The positive mode migration tube 422 and the negative mode migration tube 423 each include an ion gate 424, a migration area, a suppressor grid 427 and a Faraday's disc 428. The migration area may be composed of a string of stainless steel protective ring 425 and a ceramic insulating ring 426 which are connected in series. The sample particles with positively are detected in the positive mode migration tube, and the sample particles with negatively are detected in the negative mode migration tube.

Specifically, the carrier gas 416 from the IMS unit is ionized to generate reactive ions. The reactive ions are swept, by the carrier gas 416 from the IMS unit, into the reaction region 414 through the carrier gas inlet of the ionization region 415. In the reaction region 414, the reactive ions encounter the sample separated by the MCC 401 to produce an electrophilic reaction of adsorption, so that the sample molecules adsorb the reactive ions and thus are charged, and the positive and negative ions are guided and separated into the positive mode migration tube 422 and the negative mode migration tube 423, respectively, with the promotions of the positive and negative electrical fields of the migration tubes, and are detected by the Faraday's discs 428 at both ends. Other designs and principles of the IMS unit 412 may refer to Chinese patent application no. 200810119974.6, the contents of which will be incorporated herein by reference.

Operational process of the detection apparatus 50 according to the disclosed technology is described simply hereafter.

The detection apparatus 50 may be disposed in places such as airports, ports, subway stations, etc., and, the sample inlet of the sampling device 100 aims to an object to be inspected. Negative pressure is generated by the simulated tornado type air flow in the sampling device 100, and gaseous phase substrate or particulate substrate is suctioned into the air guide chamber 109. Through the semipermeable membrane 111, the sample and the carrier gas are mixed in the mixing area or the mixing chamber, and are discharged via the sample induction opening 120. Before the sample entering the sample pre-processing device, the thermal desorption chamber of the sample pre-processing device is maintained in a suitable constant high temperature (for example, 80° C.~300° C.). The piston-type absorber absorbed with the sample is pushed down speedy into the high temperature thermal desorption chamber, and is heated up rapidly by the adsorbents in the thermal desorption chamber so that the adsorbed sample in the absorption cavity is instantly desorbed at high temperature. The desorbed sample is mixed with the preheated carrier gas inducted through carrier gas inlet of the carrier gas inlet, and finally is carried by the carrier gas into the sample analyzing device. The sample is separated by the capillary columns in the sample analyzing device, and then is transmitted directly into the IMS unit.

The previous description of the disclosed examples is provided to enable any person skilled in the art to make or use the present invention. Various modifications to these examples will be readily apparent to those skilled in the art, and the generic principles defined herein may be applied to other examples without departing from the spirit or scope of the invention. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope. Thus, the present invention is not intended to be limited to the examples shown herein but is to be accorded the widest scope consistent with the principles and novel features disclosed herein.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

What is claimed is:

1. A detection apparatus comprising:
a sampling device for collecting a sample to be detected;
a sample pre-processing device configured to pre-process the sample from the sampling device; and
a sample analyzing device for separating the sample pre-processed by the sample pre-processing device and analyzing the separated sample,
wherein the sampling device comprises a chamber body having a sample inlet that is at a first end of the chamber body and is for suction of the sample and a sample outlet that is adjacent to a second end, opposite to the first end, of the chamber body and is for discharge of the sample,
wherein, a section of the chamber body has an inner wall with a truncated conical shape, the truncated conical shaped inner wall having a smaller-diameter round end being adjacent to the sample inlet and a larger-diameter round end being adjacent to the sample outlet of the chamber body, a cross sectional diameter of the truncated conical shaped inner wall being increasing from the smaller-diameter round end to the larger-diameter round end;
wherein the chamber body further comprises: an air inflation opening configured to induct a flow of air into the chamber body, and an air exhaust opening configured to discharge the air and to, together with the air inflation opening in the chamber body, form a tornado type air flow moving spirally from the first end to the second end of the chamber body,
and wherein the air inflation opening is configured such that an axially air induction direction of the air inflation opening is close to be in tangency with an inner surface of the inner wall of the chamber body but is inclined towards a side of the sample outlet.

2. The detection apparatus according to claim 1, wherein, the air exhaust opening is configured to discharge a peripheral gas of the tornado type air flow formed within the chamber body.

3. The detection apparatus according to claim 2, wherein, an open oriented direction, of the air exhaust opening is close to a direction that is opposed to a velocity direction of the air flow at the air exhaust opening.

4. The detection apparatus according to claim 1, wherein, the sampling device further comprises a mixing chamber body section provided at the second end of the chamber body, and the sample is transmitted into the mixing chamber body section and then into a detection system through a sample induction opening,
wherein, the mixing chamber body section is separated from other sections of the chamber body via a semi-permeable membrane,
wherein, the mixing chamber body section is provided with a carrier gas passage through which a carrier gas, for being mixing with the sample, is injected into the mixing chamber body section.

5. A detection apparatus comprising:
a sampling device for collecting a sample to be detected and having a chamber body comprising a sample inlet configured to pass a flow of air into the chamber body towards a sample outlet configured for discharge of the sample, wherein the chamber body includes a first wall portion adjacent to the sample inlet that forms a funnel extending into the chamber body, wherein the chamber body includes a second wall portion adjacent to the first wall portion that is cylindrical, and wherein an angle between the first wall portion and second wall portion causes the flow of air to form a tornado within the chamber body,
wherein the chamber body further includes an air inflation opening configured to induct a flow of air into the chamber body, and an air exhaust opening configured to discharge the air and to, together, with the air inflation opening in the chamber body, form the tornado which moves spirally from the sample inlet to the sample outlet of the chamber body;
a sample pre-processing device configured to pre-process the sample and analyze pre-processed sample.

* * * * *

UNITED STATES PATENT AND TRADEMARK OFFICE
CERTIFICATE OF CORRECTION

PATENT NO. : 10,281,432 B2
APPLICATION NO. : 15/280744
DATED : May 7, 2019
INVENTOR(S) : Qingjun Zhang It is certified that error appears in the above-identified patent and that said Letters Patent is hereby corrected as shown below:

In the Claims

Column 26, Line 1, in Claim 3, change "wherein," to --wherein--.

Column 26, Line 2, in Claim 3, change "direction," to --direction--.

Column 26, Line 38 (approx.), in Claim 5, after "analyze" insert --the--.

Signed and Sealed this
Eleventh Day of February, 2020

Andrei Iancu
*Director of the United States Patent and Trademark Office*